United States Patent
Chandraratna et al.

(10) Patent No.: US 9,271,946 B2
(45) Date of Patent: Mar. 1, 2016

(54) USE OF A RAR ANTAGONIST OR INVERSE AGONIST FOR THE TREATMENT OF CHEMOTHERAPY AND/OR RADIATION THERAPY SIDE EFFECTS

(75) Inventors: Roshantha A. Chandraratna, Laguna Hills, CA (US); Yang-Dar Yuan, Irvine, CA (US)

(73) Assignee: IO Therapeutics, Inc., Laguna Hills, CA (US)

( * ) Notice: Subject to any disclaimer, the term of this patent is extended or adjusted under 35 U.S.C. 154(b) by 1885 days.

(21) Appl. No.: 12/291,994

(22) Filed: Nov. 13, 2008

(65) Prior Publication Data

US 2009/0176862 A1 Jul. 9, 2009

Related U.S. Application Data

(63) Continuation-in-part of application No. PCT/US2007/011730, filed on May 16, 2007.

(60) Provisional application No. 60/800,773, filed on May 16, 2006.

(51) Int. Cl.
| | |
|---|---|
| *A61K 31/38* | (2006.01) |
| *A61K 31/015* | (2006.01) |
| *A61K 31/167* | (2006.01) |
| *A61K 31/192* | (2006.01) |
| *A61K 31/202* | (2006.01) |
| *A61K 31/353* | (2006.01) |
| *A61K 31/382* | (2006.01) |
| *A61K 31/44* | (2006.01) |
| *A61K 31/4436* | (2006.01) |
| *A61K 31/47* | (2006.01) |

(52) U.S. Cl.
CPC .............. *A61K 31/015* (2013.01); *A61K 31/167* (2013.01); *A61K 31/192* (2013.01); *A61K 31/202* (2013.01); *A61K 31/353* (2013.01); *A61K 31/382* (2013.01); *A61K 31/44* (2013.01); *A61K 31/4436* (2013.01); *A61K 31/47* (2013.01)

(58) Field of Classification Search
USPC .................................................. 514/432, 621
See application file for complete search history.

(56) References Cited

U.S. PATENT DOCUMENTS

| | | | |
|---|---|---|---|
| 5,728,846 A | 3/1998 | Vuligonda et al. | |
| 5,739,338 A | 4/1998 | Beard et al. | |
| 5,763,635 A | 6/1998 | Vuligonda et al. | |
| 5,773,594 A | 6/1998 | Johnson et al. | |
| 5,776,699 A | 7/1998 | Klein et al. | |
| 5,877,207 A | 3/1999 | Klein et al. | |
| 5,919,970 A | 7/1999 | Song et al. | |
| 5,952,345 A | 9/1999 | Klein et al. | |
| 5,958,954 A | 9/1999 | Klein et al. | |
| 5,998,655 A | 12/1999 | Vuligonda et al. | |
| 6,008,204 A | 12/1999 | Klein et al. | |
| 6,037,488 A | 3/2000 | Song et al. | |
| 6,043,381 A | 3/2000 | Vuligonda et al. | |
| 6,087,505 A | 7/2000 | Vuligonda et al. | |
| 6,090,810 A | 7/2000 | Klein et al. | |
| 6,117,987 A | 9/2000 | Johnson et al. | |
| 6,211,385 B1 | 4/2001 | Vuligonda et al. | |
| 6,218,128 B1 | 4/2001 | Klein et al. | |
| 6,225,494 B1 | 5/2001 | Song et al. | |
| 6,228,848 B1 | 5/2001 | Klein et al. | |
| 6,235,923 B1 | 5/2001 | Song et al. | |
| 6,313,168 B1 | 11/2001 | Pacifici et al. | |
| 6,521,624 B1 | 2/2003 | Klein et al. | |
| 6,521,641 B1 | 2/2003 | Klein et al. | |
| 6,538,149 B1 | 3/2003 | Vuligonda et al. | |
| 6,555,690 B2 | 4/2003 | Johnson et al. | |
| 6,653,483 B1 | 11/2003 | Johnson et al. | |
| 6,720,425 B2 | 4/2004 | Johnson et al. | |
| 6,818,775 B2 | 11/2004 | Johnson et al. | |
| 6,942,980 B1 | 9/2005 | Klein et al. | |
| 7,105,566 B2 * | 9/2006 | Chandraratna et al. | 514/434 |
| 7,166,726 B2 | 1/2007 | Vuligonda et al. | |
| 2002/0156054 A1 | 10/2002 | Klein et al. | |
| 2002/0173631 A1 | 11/2002 | Johnson et al. | |
| 2002/0193403 A1 | 12/2002 | Yuan et al. | |
| 2003/0219832 A1 | 11/2003 | Klein et al. | |
| 2005/0171151 A1 | 8/2005 | Yuan et al. | |

(Continued)

FOREIGN PATENT DOCUMENTS

| | | |
|---|---|---|
| WO | 94/14777 A1 | 7/1994 |
| WO | 97/09297 | 3/1997 |
| WO | 99/33821 | 7/1999 |

(Continued)

OTHER PUBLICATIONS

Walkley et al., Leukemia, 16(9): 1763-72, 2002.*
Johnson, A., et al., "Synthesis and Biological Activity of High-Affinity Retinoic Acid Receptor Antagonists", *Bioorganic & Medicinal Chemistry*, vol. 7, No. 7, pp. 1321-1338, Elsevier Science Ltd., Jul. 1999.
Teng, M., et al., "Identification of Highly Potent Retinoic Acid Receptor Alpha-Selective Antagonists", *Journal of Medicinal Chemistry*, vol. 40, pp. 2445-2451, Elsevier Science Ltd., 1997. (month of publication not available).
Walkley, C.R., et al., "Retinoic acid receptor antagonism in vivo expands the numbers of precursor cells during granulopoiesis", *Leukemia*, vol. 16, No. 9, pp. 1763-1772, Nature Publishing Group, Sep. 2002.

(Continued)

Primary Examiner — Rei-Tsang Shiao
(74) Attorney, Agent, or Firm — K&L Gates, LLP; Louis Cullman; Michelle Glasky Bergman

(57) ABSTRACT

A method for treating chemo therapy or radiation therapy side effects in a mammal undergoing chemotherapy and/or radiation therapy, the method comprising a step of administering to the mammal a therapeutically effective amount of a RAR antagonist or RAR inverse agonist which binds to receptors of the RARα, RARβ and RARγ subtypes is disclosed. Such side effects include chemoradiotherapy-induced alopecia, chemoradiotherapy-induced thrombocytopenia, chemoradiotherapy-induced leucopenia and chemoradiotherapy-induced neutropenia.

10 Claims, 7 Drawing Sheets

(56) References Cited

U.S. PATENT DOCUMENTS

2007/0054882 A1  3/2007  Klein et al.
2007/0265449 A1  11/2007  Vuligonda et al.

FOREIGN PATENT DOCUMENTS

| WO | 02/089781 | 11/2002 |
|---|---|---|
| WO | WO 02/089842 A | 11/2002 |
| WO | WO 03/062369 A | 7/2003 |
| WO | WO 03/078567 A2 | 9/2003 |
| WO | WO 03/101928 A | 12/2003 |
| WO | WO 2004/046096 A | 6/2004 |

OTHER PUBLICATIONS

May 2, 2008, International Search Report, PCT/US2007/011730.

Klein et al. "Identification and Functional Separation of Retinoic Acid Receptor Neutral Antagonists and Invesre Agonists." The Journal of Biological Chemistry, vol. 271, No. 37, pp. 22692-22696, 1996.

Mangelsdorf et al. "Characterization of three RXR genes that mediate the action of 9-cis retinoic acid." Genes and Development 6:329-344, 1992.

* cited by examiner

● : Cyclophosphamide (200 mg/kg; day 0);
○ : Cyclophosphamide (200 mg/kg; day 0) + VTP194310 (1 mg/kg; days - 4 to - 1);
△ : Cyclophosphamide (200 mg/kg; day 0) + VTP194310 (1 mg/kg; days 0 to 3);
□ : Cyclophosphamide (200 mg/kg; day 0) + VTP194310 (1 mg/kg; days 4 to 7);
■ : Cyclophosphamide (200 mg/kg; day 0) + Peg-G-CSF (10 µg/kg; day 2);
* denotes $p$ values < 0.05 (statistically significant);
** denotes $p$ values < 0.01 (statistically very significant)

●: Cyclophosphamide (200 mg/kg; day 0);
○: Cyclophosphamide (200 mg/kg; day 0) + VTP194310 (1 mg/kg; days -1 to 2);
* denotes $p$ values < 0.05 (statistically significant);
** denotes $p$ values < 0.01 (statistically very significant)

● : Control mice infected with 2.5 x $10^6$ CFU *S. aureus*.
▲ : Control mice infected with 4.1 x $10^6$ CFU *S. aureus*.
○ : VTP194310 treated mice infected with 2.5 x $10^6$ CFU *S. aureus*.
△ : VTP194310 treated mice infected with 4.1 x $10^6$ CFU *S. aureus*.

USE OF A RAR ANTAGONIST OR INVERSE AGONIST FOR THE TREATMENT OF CHEMOTHERAPY AND/OR RADIATION THERAPY SIDE EFFECTS

RELATED APPLICATIONS

This application is a continuation-in-part of International Application No. PCT/US2007/011730 which designated the United States and was filed on May 16, 2007, published in English, which claims the benefit of U.S. Provisional Application No. 60/800,773, filed May 16, 2006. The entire teachings of these applications are incorporated herein by reference.

BACKGROUND OF THE INVENTION

1. Technical Field

The present invention generally relates to methods for treating the side effects of chemotherapy and radiation therapy in mammals.

2. Description of the Related Art

Generally, normal cells in a mammal grow and divide in an orderly and controlled manner. Cancer is a disease where cells become abnormal (cancerous cells) and begin to multiply without control to develop into an extra mass of tissue called a tumor. These cancerous cells can invade nearby tissue and spread through the blood stream and lymphatic system to other parts of the body.

Presently, the four primary types of cancer treatments are immunotherapy, surgery, radiation therapy, and chemotherapy. These cancer treatments may be applied alone or in conjunction with one another. Accordingly, a cancer patient may undergo one or more treatments at a time. A single treatment could span a period of time with therapies delivered at various time intervals. Immunotherapy attempts to stimulate or restore the ability of the immune system to fight the disease. It may also be used to lessen immune-system-related side effects that may be caused by some cancer treatments. Surgery seeks to directly remove the tumor from the body.

Radiation therapy, also known as radiotherapy, uses high-energy radiation from x-rays, gamma rays, neutrons, and other sources to kill cancer cells and shrink tumors by damaging the cells' genetic material. While cancerous cells are damaged permanently and eventually die, normal cells that are damaged in radiation therapy are able to repair themselves. Side effects that can occur during radiation therapy include skin irritation and hair loss in the area being treated, as well as damage to the bone marrow.

Chemotherapy uses cytotoxic drugs, alone or in combination, to destroy cancer cells. As in radiation therapy, cancer cells can be damaged and eventually die, but healthy cells affected in the process can repair themselves after chemotherapy. Cytotoxic drugs work by interfering with the ability of a growing cell to divide and reproduce itself. Thus, in addition to cancerous cells, other normal fast-dividing, growing cells can also be affected. For example, there can be an effect on blood cells formed in the bone marrow, causing bone marrow suppression. There can also be an effect on cells in, for example, the digestive tract, in the lining of the mouth, and in the reproductive system, causing diarrhea and mouth soreness; there can also be an effect on hair follicles, causing hair loss.

Bone marrow suppression is one of the many side effects of chemotherapy and radiation therapy. It results in reduced blood cell production, including red blood cells, white blood cells, and platelets. Consequently, a patient can experience fatigue from anemia, become more susceptible to infections, from leukopenia, and bruise easily and bleed more when getting a cut, from thrombocytopenia. Drugs are typically used to counter the bone marrow suppression side effect. For example, Epogen® (epoietin α) has been used to counter the side effect of anemia in cancer chemotherapy, and WinRho® SDF ($Rh_o$ (D) immune globulin) has been used to counter the side effects of thrombocytopenia.

Prevention of, or protection from, the side effects of chemotherapy and radiation therapy would be a great benefit to cancer patients. The many previous efforts to reduce these side effects have been largely unsuccessful. For life-threatening side effects, efforts have concentrated on altering the dose and schedules of the chemotherapeutic and radiotherapeutic agents to reduce the side effects. Other options are becoming available, such as the use of granulocyte colony stimulating factor (G-CSF), granulocyte-macrophage-CSF (GM-CSF), epidermal growth factor (EGF), interleukin 11 (il-11), erythropoietin, thrombopoietin, megakaryocyte development and growth factor, pixykines, stem cell factor, FLT-ligand, as well as interleukins 1, 3, 6, and 7, to increase the number of normal cells in various tissues before the start of chemoradiotherapy. The mechanisms of protection by these factors, while not fully understood, are most likely associated with an increase in the number of normal critical target cells before treatment with cytotoxic agents or radiation therapy, and not associated with increased survival of cells following chemoradiotherapy.

Generally, neutrophils, also called polymorphonuclear leukocytes, are the most numerous of the blood cells known as granulocytes. Neutrophils are the largest cell population involved in acute inflammatory response. They are thus an important component of natural immunity, responding quickly to chemotactic stimuli. Neutrophils destroy foreign particles such as bacteria by enveloping and digesting them, a process called phagocytosis. Neutrophils may increase in response to bacterial infection. When many neutrophils are needed, they are released from the bone marrow as immature cells, called bands or stab cells. Neutropenia is a hematological disorder characterized by an abnormally low number of neutrophil granulocytes. Therefore, patients with neutropenia are more susceptible to bacterial infections, and these conditions may become life-threatening.

Neutropenia may occur secondary to another condition such as cancer or Acquired Immunodeficiency Syndrome (AIDS). Neutropenia may also occur secondary to an event such as a drug therapy. Thus, neutropenia may result from physiological disorders that directly affect the immune system. For example, diminished neutrophil production will result when leukemia, myeloma, lymphoma or a metastatic solid tumor such as, for example, breast or prostate cancer, infiltrate and replace bone marrow. Transient neutropenia is often associated with viral infections. Chronic neutropenia is often associated with immunodeficiency resulting from a viral infection, for example, AIDS resulting from infection with Human Immunodeficiency Virus (HIV). Autoimmune neutropenia may be associated with circulating anti-neutrophil antibodies.

A much more common cause of neutropenia is as a side effect of drug therapy, particularly chemotherapy and radiation therapy for cancer and bone marrow transplantation associated with cancer therapy. Neutropenia secondary to drug therapy can thus be subdivided into two groups. The first involves immune-mediated neutropenia that may arise from drugs that act as haptens to stimulate antibody formation. Acute hypersensitivity reactions such as those caused by diphenylhydantoin and phenobarbital may last a few days. However, chronic hypersensitivity reactions may last for months or years.

The second area of drug-induced neutropenia involves the severe neutropenia that predictably occurs after large doses of cytoreductive cancer drugs or ionizing radiation therapy. These cytotoxic therapies induce neutropenia because of the proliferative nature of neutrophil precursor cells and the normal rapid turnover rate of circulating neutrophils. The risk of neutropenia secondary to cancer chemotherapy or radiotherapy depends on such factors as the type and stage of the cancer and the type, the dosage and the schedule of cancer treatment.

Therapy that presently exists for raising neutrophil levels consists primarily of filgrastim (Neupogen®) and more recently, pegfilgrastim (Neulasta®), a longer acting derivative of filgrastim. Filgrastim is a recombinant version of a human protein, G-CSF, that selectively stimulates the production of white blood cells. G-CSF is currently the drug of choice for neutropenia. Since both of these drugs are recombinant proteins they are not active orally and must be administered by injection. In addition, protein-based drugs are often subject to rapid metabolism.

Despite advances in the fields of chemotherapy and radiation therapy, prior art drugs and methods have proven to be of limited utility in minimizing side effects resulting from chemotherapy and radiation therapy such as chemotherapy-induced alopecia, radiation therapy-induced alopecia, chemotherapy-induced thrombocytopenia, radiation therapy-induced thrombocytopenia, chemotherapy-induced leukopenia, radiation therapy-induced leucopenia, chemotherapy-induced neutropenia and radiation therapy-induced neutropenia. Accordingly, it would be desirable to provide an improved method for treating such side effects of chemoradiotherapy in a mammal.

SUMMARY OF THE INVENTION

In accordance with one embodiment of the present invention, a method for treating chemotherapy and/or radiation therapy side effects in a mammal undergoing chemotherapy and/or radiation therapy is provided, the method comprising a step of administering to the mammal a therapeutically effective amount of a Retinoic Acid Receptor (RAR) antagonist or a RAR inverse agonist which binds to receptors of the RARα, RARβ and RARγ subtypes.

In accordance with a second embodiment of the present invention, a method for increasing platelet production in a mammal is provided, the method comprising a step of administering to the mammal an effective amount of a RAR antagonist or a RAR inverse agonist which binds to receptors of the RARα, RARβ and RARγ subtypes.

In accordance with a third embodiment of the present invention, a method for treating a mammal suffering from thrombocytopenia is provided, the method comprising a step of administering to the mammal a therapeutically effective amount of a RAR antagonist or a RAR inverse agonist which binds to receptors of the RARα, RARβ and RARγ subtypes.

In accordance with a fourth embodiment of the present invention, a method of treating a mammal suffering from a hematopoietic related condition is provided, the method comprising a step of administering to the mammal a therapeutically effective amount of a RAR antagonist or a RAR inverse agonist which binds to receptors of the RARα, RARβ and RARγ subtypes. Such conditions include, but are not limited to, reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, acquired immune deficiency syndrome and the like and combinations thereof.

DETAILED DESCRIPTION OF THE INVENTION

Figures 1A, 1B, 1C:
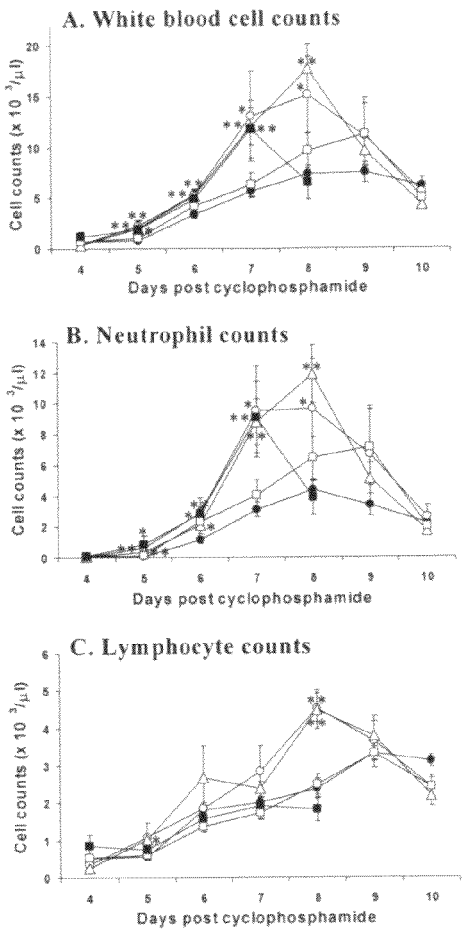
FIGS. 1A-1C are a graphical representation of the effects of VTP 194310 on the leukocyte, neutrophil and lymphocyte counts in a cyclophosphamide-induced leukopenic mouse model.

The present invention is directed to methods for the treatment of chemotherapy and/or radiation therapy (i.e., chemoradiotherapy) side effects in a mammal undergoing chemotherapy and/or radiation therapy employing at least an antagonist and/or an inverse agonist of Retinoic Acid Receptors (RARs) which binds to receptors of the RARα, RARβ and RARγ subtypes, i.e., the RAR antagonist or RAR inverse agonist binds to all of the RARα, RARβ and RARγ subtypes. Such side effects include, but are not limited to, chemotherapy-induced alopecia, radiation therapy-induced alopecia, chemotherapy-induced thrombocytopenia, radiation therapy-induced thrombocytopenia, chemotherapy-induced leukopenia, radiation therapy-induced leucopenia, chemotherapy-induced neutropenia, radiation therapy-induced neutropenia and the like and combinations thereof.

An assay that can be used to determine the agonist activity in the RARα, RARβ and RARγ receptor subtypes is described in Feigner, P. L., and Holm, M., Focus, 11:2, 21+ (1989) and U.S. Pat. Nos. 5,455,265 and 7,166,726, all of which are incorporated herein by reference in their entirety.

The activity of retinoid inverse agonists can be tested by the procedure of Klein et al., J. Biol. Chem. 271, 22692-22696 (1996) which is expressly incorporated herein by reference.

Retinoids, in particular all-trans retinoic acid (ATRA), are essential to normal mammalian development as they play important roles in controlling the survival, proliferation and differentiation of a wide range of cell types. ATRA and synthetic retinoids are capable of binding to and activating two distinct intracellular families of receptors, the RARs and the Retinoid X Receptors (RXRs), resulting in the regulation of gene expression. The first retinoic acid receptor identified, designated RARα, acts to modulate transcription of specific target genes in a manner which is ligand-dependent, as has been shown to be the case for many of the members of the steroid/thyroid hormone intracellular receptor superfamily. The endogenous low-molecular-weight ligand upon which the transcription-modulating activity of RARα depends is ATRA. Retinoic acid receptor-mediated changes in gene expression result in characteristic alterations in cellular phenotype, with consequences in many tissues manifesting the biological response to ATRA. Two additional genes closely related to RARα are designated as RARβ and RARγ. As with the RARs, the RXRs are also known to have at least three subtypes or isoforms, namely RXRα, RXRβ, and RXRγ, with corresponding unique patterns of expression (Manglesdorf et al., Genes & Devel., 6: 329-44 (1992)).

It is believed that the administration of a composition comprising a RAR antagonist and/or a RAR inverse agonist that binds to receptors of the RARα, RARβ and RARγ subtypes to a mammal may improve the production of blood neutrophils and platelets thereby resulting in the treatment of side effects of chemotherapy such as chemotherapy-induced neutropenia and/or thrombocytopenia.

Representative examples of RAR antagonists and inverse agonists that bind to receptors of the RARα, RARβ and RARγ subtypes and processes for their preparation are well known in the art, e.g., in U.S. Pat. Nos. 5,776,699 and 5,958,954 and U.S. Patent Application Publication No. 2002/0193403, the contents of each of which are incorporated by reference herein in their entirety. Many of the following compounds are included in one or more of these applications and/or patents.

A particular embodiment of the present invention is a class of compounds that may be used is represented by the general formula I:

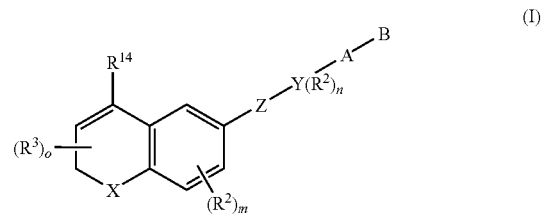

or a pharmaceutically acceptable salt thereof;
wherein X is S, O, NR where R is H or alkyl of 1 to 6 carbons, or
X is $[C(R^1)_2]_n$ where $R^1$ is independently H or an alkyl of 1 to 6 carbons, and n is an integer between, and including, 0 and 2;
$R^2$ independently are hydrogen, a lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;
$R^3$ independently are hydrogen, lower alkyl of 1 to 6 carbons or F;
m is an integer having the value of 0-3;
n is an integer having the value of 0-4;
o is an integer having the value of 0-3;
Z is —$CONR^1$—, —$CSNR^1$—, —$NR^1CO$—, —$NR^1CS$—, —C≡C—, —C=C—, —N=N—, —N=$CR^1$—, —$CR^1$=N—, —COO—, —OCO—; —OSO—; —OCS—, or —$(CR^1=CR^1)_{n'}$— where n' is an integer from 0 to 5;
Y is a phenyl or naphthyl group, or a heteroaryl selected from a group consisting of pyridyl, thienyl, furyl, pyridazinyl, pyrimidinyl, pyrazinyl, thiazolyl, oxazolyl, imidazolyl and pyrazolyl, the phenyl and heteroaryl groups being optionally substituted with one or two $R^2$ groups, or when Z is —$(CR_1=CR_1)_{n'}$— and n' is 3, 4 or 5 then Y represents a direct valence bond between said $(CR_2=CR_2)_{n'}$ group and B;
A is $(CH_2)_q$ where q is 0-5, a lower branched chain alkyl having 3 to 6 carbons, cycloalkyl having 3 to 6 carbons, alkenyl having 2 to 6 carbons and 1 or 2 double bonds, alkynyl having 2-6 carbons and 1 or 2 triple bonds;
B is hydrogen, COOH or a pharmaceutically acceptable salt thereof, $COOR^8$, $CONR^9R^{10}$, $CH_2OH$, $CH_2OR^{11}$, $CH_2OCOR^{11}$, CHO, $CH(OR^{12})_2$, $CHOR^{13}O$, —$COR^7$, $CR^7(OR^{12})_2$, $CR^7OR^{13}O$, or a tri-lower alkylsilyl;
$R^7$ is an alkyl, cycloalkyl or alkenyl group containing 1 to 5 carbons;
$R^8$ is an alkyl group of 1 to 10 carbons or trimethylsilylalkyl where the alkyl group has 1 to 10 carbons, a cycloalkyl group of 3 to 10 carbons, phenyl or a lower alkylphenyl;
$R^9$ and $R^{10}$ independently are hydrogen, an alkyl group of 1 to 10 carbons, a cycloalkyl group of 3 to 10 carbons, phenyl or a lower alkylphenyl;
$R^{11}$ is a lower alkyl, phenyl or lower alkylphenyl;
$R^{12}$ is a lower alkyl;
$R^{13}$ is a divalent alkyl radical of 2 to 5 carbons;
$R^{14}$ is $(R^{15})_r$-phenyl, $(R^{15})_r$-naphthyl, or $(R^{15})_r$-heteroaryl wherein the heteroaryl group has 1 to 3 heteroatoms selected from the group consisting of O, S and N, and r is an integer having the values of 0-5; and
$R^{15}$ is independently H, F, Cl, Br, I, $NO_2$, $N(R^8)_2$, $N(R^8)COR^8$, $NR^8CON(R^8)_2$, OH, $OCOR^8$, $OR^8$, CN, an alkyl group having 1 to 10 carbons, a fluoro substituted alkyl group having 1 to 10 carbons, an alkenyl group having 2 to 10 carbons and 1 to 3 double bonds, an alkynyl group having 2 to 10 carbons and 1 to 3 triple bonds, or a trialkylsilyl or trialkylsilyloxy group where the alkyl groups independently have 1 to 6 carbons.

Another particular embodiment of the present invention is a class of compounds that may be used is represented by Formula I, wherein Z is —CONR$^1$—, —CSNR$^1$—, —NR$^1$CO—, or —NR$^1$CS—; and wherein all other variables are as defined above.

Another particular embodiment of the present invention is a class of compounds that may be used is represented by the Formula I, wherein:

R$^8$ is an alkyl group of 1 to 10 carbons or trimethylsilylalkyl where the alkyl group has 1 to 10 carbons, a cycloalkyl group of 5 to 10 carbons, phenyl or a lower alkylphenyl;

R$^9$ and R$^{10}$ independently are hydrogen, an alkyl group of 1 to 10 carbons, a cycloalkyl group of 5 to 10 carbons, phenyl or a lower alkylphenyl; and wherein all other variables are as defined above.

Another particular embodiment of the present invention is a class of compounds that may be used is represented by the general formula II:

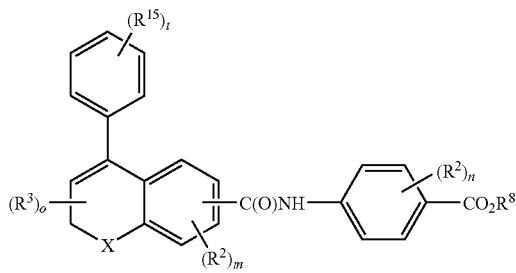

(II)

or a pharmaceutically acceptable salt of the compound;
wherein X is —C(R$^1$)$_2$— or —O—; R$^1$ is H or C$_1$-C$_6$ alkyl;
R$^2$ is a lower C$_1$-C$_6$ alkyl, —F, —Cl, —Br, —I, —CF$_3$, fluoro substituted C$_1$-C$_6$ alkyl, —OH, —SH, C$_1$-C$_6$ alkoxy, or C$_1$-C$_6$ alkylthio;
m is an integer from 0 to 3;
n is an integer from 0 to 4;
o is an integer from 0 to 3;
R$^3$ is a lower C$_1$-C$_6$ alkyl or —F;
R$^8$ is a C$_1$-C$_{10}$ alkyl, C$_1$-C$_{10}$ trimethylsilylalkyl, a C$_3$-C$_{10}$ cycloalkyl, phenyl or a lower alkylphenyl;
each is R$^{15}$ independently —H, —F, Cl, —Br, —I, —NO$_2$, —N(R$^8$)$_2$, —COR$^8$, —NR$^8$CON(R$^8$)$_2$, —OCOR$^8$, —OR$^8$, —CN, a C$_1$-C$_{10}$ alkyl, fluoro substituted C$_1$-C$_{10}$ alkyl, a C$_2$-C$_{10}$ alkenyl having 1 to 3 double bonds, a C$_2$-C$_{10}$ alkynyl having 1 to 3 triple bonds, or a C$_1$-C$_6$ trialkylsilyl or trialkylsilyloxy;
t is an integer from 0 to 5; and
the —CONH group is in the 6 or 7 position of the benzopyran and of the dihydronaphthaline ring.

Another particular embodiment of the present invention is a class of compounds that may be used is represented by the general Formula II, wherein:

R$^2$ is F; R$^8$ is an alkyl group of 1 to 10 carbons, trimethylsilylalkyl wherein the alkyl group has 1 to 10 carbons, or a cycloalkyl group of 5 to 10 carbons, phenyl or a lower alkylphenyl; and
R$^{15}$ independently is H, F, Cl, Br, I, NO$_2$, N(R$^8$)$_2$, COR$^8$, NR$^8$CON(R$^8$)$_2$, OCOR$^8$, OR$^8$, CN, an alkyl group having 1 to 10 carbons, fluoro substituted alkyl group having 1 to carbons, an alkenyl group having 1 to 10 carbons and 1 to 3 double bonds, an alkynyl group having 1 to 10 carbons and 1 to 3 triple bonds, or a trialkylsilyl or trialkylsilyloxy group where the alkyl groups independently have 1 to 6 carbons; and wherein all other variables are as defined above.

Another particular embodiment of the present invention is a class of compounds that may be used is represented by the general Formula III:

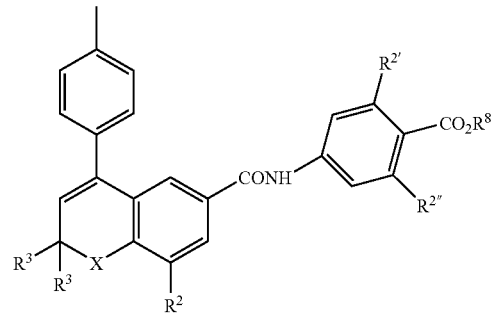

(III)

or a pharmaceutically acceptable salt thereof;
wherein X is —C(CH$_3$)$_2$— or —O—;
R$^2$ is —H or —Br,
R$^{2'}$ and R$^{2''}$ are independently —H or —F;
each R$^3$ is independently —H or —CH$_3$; and
R$^8$ is —H, or a C$_1$-C$_6$ alkyl.

Another particular embodiment of the present invention is a class of compounds that may be used is represented by the general Formula IV:

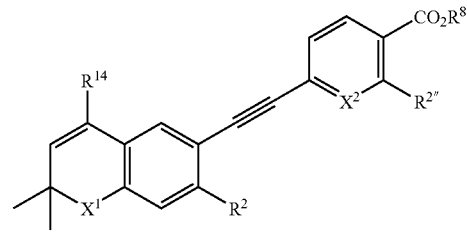

(IV)

or a pharmaceutically acceptable salt thereof,
wherein X$^1$ is —S— or —O—;
X$^2$ is —CH— or —N—;
R$^2$ is —H, —F, —CF$_3$ or C$_1$-C$_6$ alkoxy;
R$^{2''}$ is —H, —F, or —CF$_3$;
R$^8$ is —H, or C$_1$-C$_6$ alkyl;
R$^{14}$ is an unsubstituted phenyl, thienyl or pyridyl, or phenyl, thienyl or pyridyl that are substituted with one to three R$^{15}$ groups; and
each instance of R$^{15}$ is independently a C$_1$-C$_6$ alkyl, —Cl, —CF$_3$, or a C$_1$-C$_6$ alkoxy.

Another particular embodiment of the present invention is a class of compounds that may be used is represented by the general Formula V:

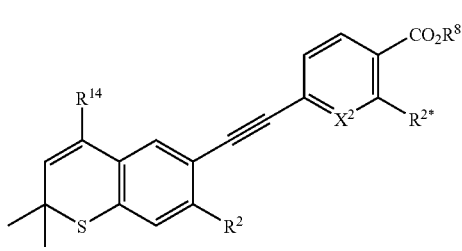

(V)

or a pharmaceutically acceptable salt thereof;
wherein $X^2$ is —CH— or —N—;
$R^2$ is —H, —F, or —OCH$_3$;
$R^{2*}$ is —H or —F;
$R^8$ is —H, or $C_1$-$C_6$ alkyl; and
$R^{14}$ is selected from the group consisting of: phenyl, 4-(lower-alkyl)phenyl, 5-(lower-alkyl)-2-thienyl, and 6-(lower-alkyl)-3-pyridyl, where lower alkyl has 1 to 6 carbons.

Another particular embodiment of the present invention is a class of compounds that may be used is represented by the general Formula VI:

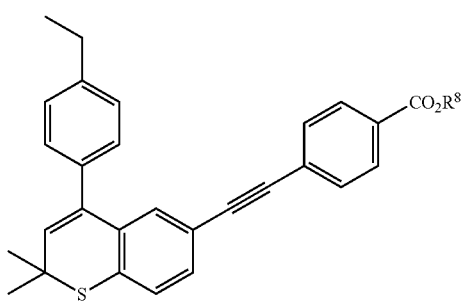

(VI)

or a pharmaceutically acceptable salt thereof;
wherein $R^8$ is —H, or a $C_1$-$C_6$-alkyl.

Another particular embodiment of the present invention is a class of compounds that may be used is represented by the general Formula VII:

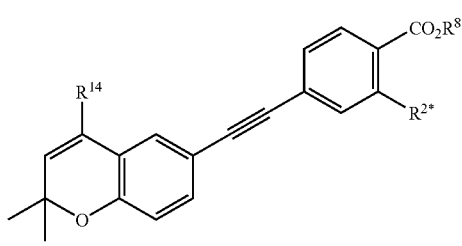

(VII)

or a pharmaceutically acceptable salt thereof;
wherein $R^{2*}$ is —H or —F;
$R^8$ is —H, or a $C_1$-$C_6$-alkyl; and
$R^{14}$ is selected from the group consisting of: phenyl, and 4-($C_1$-$C_6$-alkyl)phenyl.

Another particular embodiment of the present invention is a class of compounds that may be used is represented by the general Formula VIII:

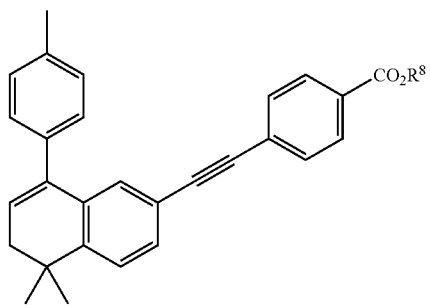

(VIII)

or a pharmaceutically acceptable salt thereof;
wherein $R^8$ is H, or a $C_1$-$C_6$-alkyl. When $R^8$ is H, this compound is termed AGN 193109.

Another particular embodiment of the present invention is a class of compounds that may be used is represented by the general formula IX:

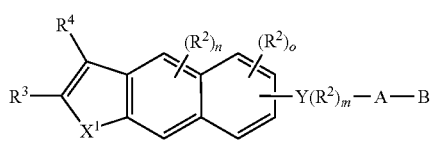

(IX)

or a pharmaceutically acceptable salt thereof;
wherein $X^1$ is —C(R$^1$)$_2$—, —C(R$^1$)$_2$—C(R$^1$)$_2$—, —S—, —O—, —NR$^1$—, —C(R$^1$)$_2$—O—, —(C(R$^1$)$_2$—S—, or —C(R$^1$)$_2$—NR$^1$—; wherein each $R^1$ is independently H or a $C_1$-$C_6$-alkyl;
each $R^2$ is independently a $C_1$-$C_6$-alkyl, —F, —Cl, —Br, —I, —CF$_3$, fluoro substituted $C_1$-$C_6$-alkyl, —OH, —SH, $C_1$-$C_6$-alkoxy, or $C_1$-$C_6$-alkylthio;
m is an integer from 0 to 4;
n is an integer from 0 to 2;
o is an integer from 0 to 3;
$R^3$ is —H, $C_1$-$C_6$-alkoxy, —F, —Cl, —Br, or —I;
$R^4$ is (R$^5$)$_p$-phenyl, (R$^5$)$_p$-naphthyl, or (R$^5$)$_p$-heteroaryl, wherein the heteroaryl group is five-membered or 6-membered and has 1 to 3 heteroatoms selected from the group consisting of oxygen, sulfur and nitrogen; wherein p is an integer from 0 to 5;
each $R^5$ is independently —F, —Cl, —Br, —I, —NO$_2$, —N(R$^8$)$_2$, —N(R$^8$)COR$^8$, —N(R$^8$)CON(R$^8$)$_2$, —OH, —OCOR$^8$, —OR$^8$, —CN, —COOH, —COOR$^8$, $C_1$-$C_{10}$-alkyl, a $C_1$-$C_{10}$-alkenyl having 1 to three double bonds, $C_1$-$C_{10}$-alkynyl having 1 to 3 triple bonds, $C_1$-$C_6$-(trialkyl)silyl or $C_1$-$C_6$-(trialkyl)silyloxy;
Y is a phenyl, naphthyl, or a heteroaryl selected from the group consisting of: pyridyl, thienyl, furyl, pyridazinyl, pyrimidinyl, pyrazinyl, thiazolyl, oxazolyl, imidazolyl and pyrazolyl; wherein said phenyl and heteroaryl groups are optionally and independently substituted with one or two $R^2$ groups, or Y is a —(CR$^3$=CR$^3$)$_r$—;
r is an integer from 1 to 3;
A is (CH$_2$)$_q$, a lower $C_3$-$C_6$ branched chain alkyl, $C_3$-$C_6$ cycloalkyl having, $C_2$-$C_6$ is alkenyl having 1 or 2 double bonds, $C_2$-$C_6$ alkenyl having 1 or 2 triple bonds; wherein q is an integer from 0 to 5, and with the proviso that when Y is —(CR$_3$=CR$_3$)$_r$—, then A is (CH$_2$)$_q$ and q is 0;
B is —H, —COOH, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or —Si(C$_{1-6}$alkyl)$_3$;

R$^7$ is an alkyl, cycloalkyl or alkenyl group containing 1 to 5 carbons;

R$^8$ is a C$_1$-C$_{10}$ alkyl group, C$_1$-C$_{10}$ (trimethylsilyl)alkyl, or a C$_5$-C$_{10}$ cycloalkyl, phenyl or lower alkylphenyl;

R$^9$ and R$^{10}$ are each independently —H, a C$_1$-C$_{10}$ alkyl, a C$_5$-C$_{10}$ cycloalkyl, phenyl or lower alkylphenyl;

R$^{11}$ is a lower alkyl, phenyl or lower alkylphenyl;

R$^{12}$ is a lower alkyl; and

R$^{13}$ is a divalent alkyl radical of 2-5 carbons.

Another particular embodiment of the present invention is a class of compounds that may be used is represented by the general formula X:

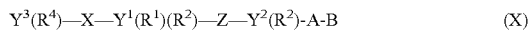

Y$^3$(R$^4$)—X—Y$^1$(R$^1$)(R$^2$)—Z—Y$^2$(R$^2$)-A-B    (X)

or a pharmaceutically acceptable salt thereof;

wherein Y$^1$ is phenyl, naphthyl, or heteroaryl selected from the group consisting of pyridyl, thienyl, furyl, pyridazinyl, pyrimidinyl, pyrazinyl, thiazonyl, ozazolyl, imidazolyl, and pyrazolyl, wherein the phenyl, naphthyl, and heteroaryl groups are optionally substituted with an R$^1$ group, and optionally further substituted with 1 or 2 R$^2$ groups;

R$^1$ is C$_1$-C$_{10}$ alkyl, 1-adamantyl, 2-tetrahydropyranoxy, C$_1$-C$_6$ trialkylsilanyloxy, —OH, C$_1$-C$_{10}$ alkoxy, C$_1$-C$_{10}$, or —OCH$_2$O—(C$_1$-C$_6$ alkyl);

R$^2$ is C$_1$-C$_6$ alkyl, —F, —Cl, —Br, —I, —CF$_3$, —CF$_2$CF$_3$, —OH, —OR$^3$, —NO$_2$, —N(R$^3$)$_2$, —CN, —N$_3$, —COR$^3$, —NHCOR$^3$, —COOH, or —COOR$^3$;

X is —(C(R$^3$)$_2$)—, —S—, —SO—, —SO$_2$—, —O—, —C(=O)—, —C(=S)—, —C(=NR$^1$)—, —C(=C(R$^1$)$_2$)— or —NR$^3$—;

Z is —C≡C—, —N=N—, —N(O)=N—, —N=N(O)—, —N=CR$^3$—, —CR$^3$=N—, —(CR$^3$=CR$^3$)$_n$—, —OCO—, —CSO—, —OCS—, —COCR$^3$=R$^{30}$—, —CO—NR$^3$—, —CS—NR$^3$—, —NR$^3$—CO—, or —NR$^3$—CS—;

n is an integer having a value of 0-5;

each R$^3$ is independently —H or a C$_1$-C$_6$ alkyl;

Y$^2$ is a phenyl or naphthyl group, or a heteroaryl selected from a group consisting of: pyridyl, thienyl, furyl, pyridazinyl, pyrimidinyl, pyrazinyl, thiazolyl, oxazolyl, imidazolyl and pyrazolyl; wherein the phenyl, naphthyl and heteroaryl groups can be unsubstituted or substituted with one or two R$^2$ groups; provided that when Z is —(CR$^3$=CR$^3$)$_n$— and n is 3, 4, or 5, then Y$^2$ represents a direct valence bond between said —(CR$^3$=CR$^3$)$_n$— group and B;

Y$^3$ is phenyl, naphthyl, or heteroaryl selected from a group consisting of: pyridyl, thienyl, furyl, pyridazinyl, pyrimidinyl, pyrazinyl, thiazolyl, oxazolyl, imidazolyl and pyrazolyl; wherein the phenyl, naphthyl and heteroaryl groups are optionally substituted with one to five R$^4$ groups;

each R$^4$ is independently a C$_1$-C$_{10}$ alkyl, C$_2$-C$_{10}$ alkenyl having 1 to 3 triple bonds, —F, —Cl, —Br, —I, —NO$_2$, N(R$^3$)$_2$, —N$_3$, —COOH, —COO—(C$_1$-C$_6$ alkyl), —OH, —SH, —O—C$_1$-C$_6$ alkyl, or —S—C$_1$-C$_6$ alkyl;

A is (CH$_2$)$_q$, a lower C$_3$-C$_6$ branched alkyl, C$_3$-C$_6$ cycloalkyl, C$_2$-C$_6$ alkenyl having 1-2 double bonds, C$_2$-C$_6$ alkynyl having 1 to 2 triple bonds; wherein q is an integer from 0-5;

B is —H, —COOH, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or —Si(C$_1$-C$_6$ alkyl)$_3$;

R$^7$ is an alkyl, cycloalkyl or alkenyl group containing 1 to 5 carbons;

R$^8$ is a C$_1$-C$_{10}$ alkyl, C$_1$-C$_{10}$ trimethylsilylalkyl, a C$_3$-C$_{10}$cycloalkyl, phenyl or lower alkylphenyl;

R$^9$ and R$^{10}$ are independently hydrogen, a C$_1$-C$_{10}$ alkyl, a C$_3$-C$_{10}$cycloalkyl, phenyl or lower alkylphenyl;

R$^{11}$ is a lower alkyl, phenyl or lower alkylphenyl;

R$^{12}$ is a lower alkyl; and

R$^{13}$ is divalent alkyl radical of 2 to 5 carbons.

Another particular embodiment of the present invention is a class of compounds that may be used is represented by the general Formula X, wherein X is —(C(R$^3$)$_2$)—, —S—, —SO—, —SO$_2$—, —O—, or —NR$^3$—; and Z is —CO—NR$^3$—, —CS—NR$^3$—, —NR$^3$—CO—, or —NR$^3$—CS—, and wherein all other variables are as defined above.

Another particular embodiment of the present invention is a class of compounds that may be used is represented by the general Formula X, wherein X is —C(=O)—, —C(=S)—, —C(=NR$^1$)—, or —C(=C(R$^1$)$_2$)—; and Z is —CO—NR$^3$—, —CS—NR$^3$—, —NR$^3$—CO—, or —NR$^3$—CS—, and wherein all other variables are as defined above.

Another particular embodiment of the present invention is a class of compounds that may be used is represented by the general Formula X wherein the phenyl, naphthyl, or heteroaryl groups represented by Y$^3$ are unsubstituted or substituted by 1-3 R$^4$ groups, and wherein all other variables are as defined above.

The present application contemplates using any compound that is a RAR antagonist or inverse agonist which binds to the receptors of the RARα, RARβ and RARγ subtypes, including the compounds described in or claimed in U.S. Pat. Nos. 5,728,846, 5,739,338, 5,763,635, 5,773,594, 5,877,207, 5,952,345, 5,958,954, 5,998,655, 6,008,204, 6,037,488, 6,043,381, 6,087,505, 6,090,810, 6,117,987, 6,211,385, 6,218,128, 6,225,494, 6,228,848, 6,235,923, 6,313,168, 6,521,624, 6,521,641, 6,538,149, 6,555,690, 6,653,483, 6,720,425, 6,818,775, 6,942,980, 7,105,566, and 7,166,726 and U.S. application Ser. Nos. 10/446,580, 11/016,534, 11/500,277, 11/503,635, 11/607,406, and 11/643,754. All of the above referenced patents and patent applications are incorporated herein by reference in their entirety.

A non-exclusive list of compounds falling within the description and methods for making this class of compounds are disclosed in U.S. Pat. No. 5,728,846, the contents of which are herein incorporated by reference. Additionally, these compounds are disclosed in U.S. patent application Ser. No. 08/840,040, Song et al., which application shares common ownership with the present application and is incorporated by reference herein in its entirety.

A preferred compound for use in the methods of the present invention is represented by the following structure:

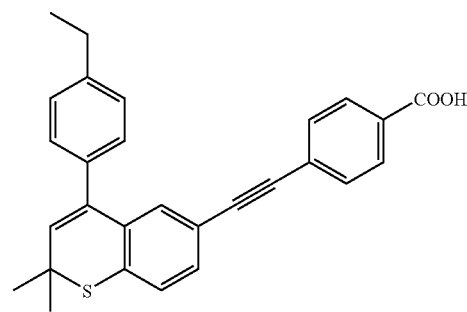 [SMILES: CCc1ccc(C2=CC(C)(C)Sc3ccc(C#Cc4ccc(C(=O)O)cc4)cc32)cc1]

or pharmaceutically acceptable salt thereof. This compound is referred to as VTP 194310 (and was formerly referred to as AGN 194310).

Another preferred compound for use in the methods of the present invention is represented by the following structure:

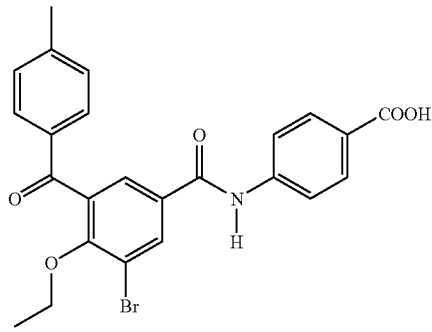 [SMILES: CCOc1c(Br)cc(C(=O)Nc2ccc(C(=O)O)cc2)cc1C(=O)c1ccc(C)cc1]

or a pharmaceutically acceptable salt thereof. This compound is referred to as VTP 196996.

Additional RAR antagonists or inverse agonists are described in U.S. patent application Ser. No. 08/845,019, Song et al. which is incorporated by reference herein in its entirety; and shares common ownership with the present application. Also, compounds useful in the methods of the present invention are disclosed in International Application Publication No. WO 94/14777, Yoshimura et al., which is also incorporated by reference herein in its entirety. This latter application discloses RAR antagonists.

Furthermore, structures of additional compounds useful in the methods of the present invention are as follows:

A

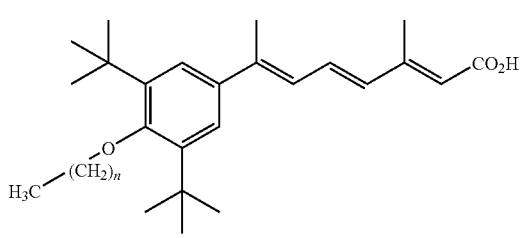

or a pharmaceutically acceptable salt thereof; wherein n is an integer from 1 to 10;

B

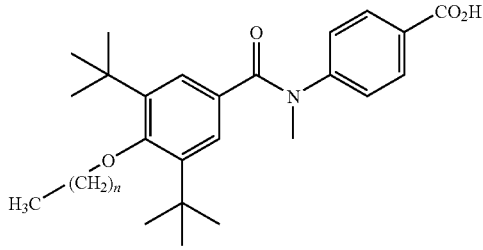

or a pharmaceutically acceptable salt thereof; wherein n is an integer from 1 to 10;

C

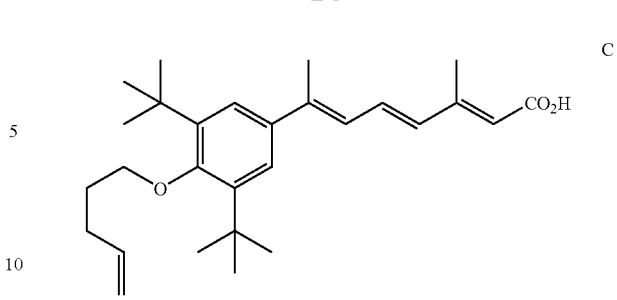

or a pharmaceutically acceptable salt thereof;

D

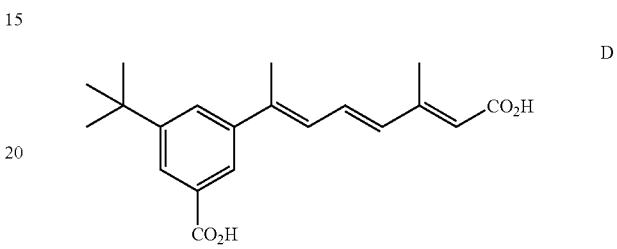

or a pharmaceutically acceptable salt thereof; and

E

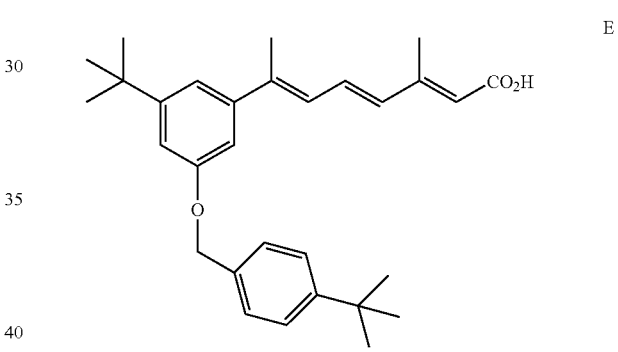

or a pharmaceutically acceptable salt thereof.

The term "agonist" as used herein shall be understood to mean a compound which binds to a receptor and activates it, producing a pharmacological response (e.g., contraction, relaxation, secretion, enzyme activation, etc.).

The term "inverse agonist" as used herein shall be understood to mean a compound which produces an effect opposite to that of an agonist, yet acts at the same receptor. The term "inverse agonist" is synonymous with the term "negative antagonist."

The term "antagonist" as used herein shall be understood to mean a compound that attenuates the effect of an agonist by binding in the same site as an agonist without activating the receptor.

The term "chemoradiotherapy" as used herein shall be understood to mean chemotherapy, radiation therapy or both.

The term "treating" or "treatment" as used herein shall be understood to mean (1) preventing, reducing the severity of or delaying the appearance of a clinical symptom of a state, disease, disorder, injury or condition developing in a mammal, partially or completely, that may be afflicted with or predisposed to the state, disease, disorder, injury or condition but does not yet experience or display clinical or subclinical symptoms of the state, disease, disorder, injury or condition, (2) inhibiting the state, disease, disorder, injury or condition partially or completely, i.e., arresting or reducing the development of the state, disease, disorder, injury or condition or at least one clinical or subclinical symptom thereof, or (3) relieving the state, or reducing the severity of the disease, disorder, injury or condition, partially or completely, i.e., causing regression of the state, disease, disorder, injury or condition or at least one clinical or subclinical symptom thereof.

The term "delivering" as used herein shall be understood to mean providing a therapeutically effective amount of a RAR antagonist or RAR inverse agonist capable of binding to receptors of the RARα, RARβ and RARγ type to a particular location within a mammal causing a therapeutically effective concentration of the RAR antagonist or RAR inverse agonist which binds to receptors of the RARα, RARβ and RARγ type at the particular location.

The term "subject" or "patient" or "host" or "mammal" as used herein refers to mammalian animals, including humans.

The term "alkyl" used alone or as part of a larger moiety, such as "alkoxy", and "hydroxyalkyl", means a saturated aliphatic containing one to ten carbon atoms. Representative saturated straight chain alkyls include methyl, ethyl, n-propyl, n-butyl, n-pentyl, and the like; while saturated branched alkyls include isopropyl, sec-butyl, isobutyl, tert-butyl, isopentyl, and the like. The term "lower alkyl" describes an alkyl containing one to six carbons. Alkenyl and alkynyl groups are unsaturated aliphatic groups and contain at least one double or triple bond between adjacent carbon atoms. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The term "cycloalkyl" means a saturated cyclic hydrocarbon moiety and include cyclopropyl, cyclobutyl, cyclopentyl, cyclohexyl. Cycloalkyls can also include carbocyclic rings systems, such as bi- and tri-cyclic ring systems having from 8 to 10 carbon atoms, such as a cycloalkyl (e.g., cyclopentane or cyclohexane) fused to one or more aromatic (such as phenyl) or non-aromatic (such as cyclohexane) carbocyclic rings.

The term "heteroaryl", "heteroaromatic", "heteroaromatic ring", and "heteroaryl group" used alone or as part of a larger moiety, refer to heteroaromatic ring groups typically having five to fourteen members, including monocyclic heteroaromatic rings and polycyclic aromatic rings in which a monocyclic heteroaromatic ring is fused to one or more other carbocyclic or heteroaromatic aromatic rings. Heteroaryl groups have one or more, typically 1, 2, or 3, ring heteroatoms, such as nitrogen, oxygen and sulfur.

"Pharmaceutical composition" of the compounds described herein, and their pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The SARM compound will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19th edition, Mack Publishing Co., Easton, Pa. (1995).

Pharmaceutically acceptable salts are also included as embodiments of the present invention.

"Pharmaceutically acceptable salt" is a salt of a compound containing any acidic or basic functional group. For example, a pharmaceutically acceptable salt of an amine or other basic group can be obtained by reacting the compound with a suitable organic or inorganic acid, such as hydrogen chloride, hydrogen bromide, acetic acid, perchloric acid and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof, including racemic mixtures], succinates, benzoates and salts with amino acids such as glutamic acid.

Pharmaceutically acceptable salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine.

The RAR antagonist and RAR inverse agonist compounds which bind to receptors of the RARα, RARβ and RARγ subtypes for use in the methods of the present invention may be incorporated into a pharmaceutical composition. All modes of administrations are contemplated, e.g., orally, rectally, parenterally, topically, or by intravenous, intramuscular, intrasternal or subcutaneous injection or in a form suitable by inhalation. The formulations may, where appropriate, be conveniently presented in discrete dosage units and may be prepared by any of the methods well known in the art of pharmacy. The compounds will ordinarily be formulated with one or more pharmaceutically acceptable ingredients in accordance with known and established practice. Thus, the pharmaceutical composition can be formulated as a liquid, powder, elixir, injectable solution, suspension, suppository, etc.

Formulations for oral use can be provided as tablets or hard capsules wherein the compounds are mixed with an inert solid diluent such as calcium carbonate, calcium phosphate or kaolin, or as soft gelatin capsules wherein the active ingredients are mixed with water or miscible solvents such as propylene glycol, PEGs and ethanol, or an oleaginous medium, e.g., peanut oil, liquid paraffin or olive oil.

For topical administration in the mouth, the pharmaceutical compositions can take the form of buccal or sublingual tablet, drops or lozenges formulated in conventional manner.

For topical administration to the epidermis, the compounds can be formulated as creams, gels, ointments or lotions or as transdermal patches. Such compositions can, for example, be formulated with an aqueous or oily base with the addition of suitable thickening, gelling, emulsifying, stabilizing, dispersing, suspending, and/or coloring agents.

The compounds can also be formulated as depot preparations. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example as a sparingly soluble salt.

The compounds can be formulated for parenteral administration by injection, conveniently intravenous, intramuscular or subcutaneous injection, for example by bolus injection or continuous intravenous infusion. Formulations for injection can be presented in unit dosage from, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the compounds may be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glyceride.

For intranasal administration, the compounds can be used, for example, as a liquid spray, as a powder or in the form of drops.

For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit can be determined by providing a valve to deliver a metered amount. Capsules and cartridges of, e.g., gelatin for use in an inhaler or insulator can be formulated containing a powder mix of the retinoid compound and a suitable powder base such as lactose or starch.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl- or -n-propyl-p-hydroxy benzoate, one or more coloring agents, one or more flavoring agents and one or more sweetening agents, such as sucrose, saccharin or sodium or calcium cyclamate.

In addition to the RAR antagonist and RAR inverse agonist compounds which bind to receptors of the RARα, RARβ and RARγ subtypes, at least one other pharmacologically active substance, e.g., a non-narcotic analgesic such as tramadol, acetaminophen, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and the like and combinations thereof, or a narcotic analgesic such as codeine, oxycodone, dihydrocodeine, hydrocodone, levorphanol, morphine and the like and combinations thereof, or other agents such as, for example, G-CSF, GM-CSF, EGF, interleukin 11, erythropoietin, thrombopoietin, megakaryocyte development and growth factor, pixykines, stem cell factor, FLT-ligand, as well as interleukins 1, 3, 6, and 7 and the like and combinations thereof can be administered with the RAR antagonist and RAR inverse agonist compounds which bind to receptors of the RARα, RARβ, and RARγ subtypes.

The compounds will be administered in a therapeutically effective amount in accordance with the invention. A therapeutic concentration will be that concentration which is effective to treat, for example, the side effects of chemoradiotherapy in a mammal, preferably a human being. These amounts can be determined by one skilled in the art.

The following are non-limiting examples of the present invention. The examples should not be read as limiting the scope of the invention as defined in the claims.

Each of the following examples use 4-2[6-(2,2-dimethyl-(1H)-4-(4-ethylphenyl)-1-benzothiopyran))ethynyl]benzoic acid (VTP 194310 and formerly termed AGN 194310) as synthesized at Allergan Inc. (Irvine, Calif.) and is a specific pan-RAR antagonist. The structure of VTP 194310 is shown hereinabove. The $K_i$ of VTP 194310 for binding to RARα, β and γ is 3, 2 and 5 nM, respectively. VTP 194310 shows no activity in transactivation assays, but instead blocks the gene transcriptional activity induced by ATRA and other RAR agonists. VTP 194310 and ATRA were stored as 10 mM stock solutions in 50% ethanol/50% dimethylsulphoxide (DMSO) at −20° C.

EXAMPLE 1

Neutrophil and Lymphocyte Recovery in a Cyclophosphamide-Induced Mouse Model of Leukopenia Mice Mice purchased from Charles River Laboratories (Wilmington, Mass.) were housed individually in micro-isolater cages in a 12-hour light/dark cycle. They were housed under pathogen-free conditions, and received a normal standard diet and water ad libitum. They were acclimated for one week at the Association for Assessment and Accreditation of Laboratory Animal Care (AAALAC) accredited animal facility (Allergan Inc., Irvine, Calif.) prior to experiments. Study designs were approved by the Institutional Animal Care and Use Committee. Body weights were monitored throughout each study. Weight of the mice was in the range of 22-27 g at the day of treatment initiation. The mice were healthy, not previously used in other experimental procedures.

In Vivo Leukopenia Model

Leukopenia was induced in male BDF1 mice (C57Bl× DBA2, 7.5-12 weeks) by an intra-peritoneal (i.p.) injection of 200 mg/kg Cyclophosphamide (CPM, Sigma-Aldrich, Saint Louis, Mo.) in 0.2 ml saline. The effect of VTP 194310 on leukocyte recovery was evaluated by oral gavage of animals with 1 mg/kg of VTP 194310 as indicated in the results section. VTP 194310 (dissolved in DMSO) was diluted through peanut oil as the vehicle (dosed at 5 ml/kg). Control mice were given DMSO and vehicle alone. As a positive control, granulocytopoiesis was stimulated in CPM-treated mice by a single sub-cutaneous injection of 10 μg/kg pegylated recombinant methionyl human granulocyte colony-stimulating factor (PEG-r-metHuG-CSF) (Neulasta, Pegfilgrastim; Amgen, Thousand Oaks, Calif.) on day 2. Three separate experiments were performed.

Peripheral blood (60 μl) was collected under anaesthesia from the retroorbital sinus of the mice with heparinized capillary tubes and transferred to EDTA-coated microtainer tubes (Becton Dickinson, Franklin Lakes, N.J.). White cell, neutrophil, and lymphocyte counts were obtained for at least three mice per group by diluting the blood 1:4 with PBS containing 5% bovine serum albumin (Fraction V; Sigma, Saint Louis, Mo.), and by using an Advia 120 Hematology System (Bayer HealthCare Diagnostics Division, Tarrytown, N.Y.).

Immature ($Gr-1^{low}/CD11b^{+ve}$) and mature ($Gr-1^{+ve}/CD11b^{+ve}$) neutrophils were identified in single cells suspensions prepared from spleen and bone marrow (femur) aspirates by double immunostaining using PE- and FITC-conjugated monoclonal antibodies (Pharmingen, San Diego, Calif.). Cells were analysed on a FACS Calibur interfaced with CellQuest Pro software program (Becton Dickinson, San Jose, Calif.).

Results

As the data show, the use of VTP 194310 improved leukocyte recovery in a cyclophosphamide-induced mouse model of leucopenia. Treatment of mice with a single dose of CPM at 200 mg/kg resulted in a profound leukopenia and neutropenia at day 4. Leukocyte and neutrophil counts in the blood of CPM-treated mice were $0.69\pm0.09$ $(SEM)\times10^3/\mu l$ and $0.09\pm0.02\times10^3/\mu l$, respectively, as compared to values of $8.98\pm0.33\times10^3/\mu l$ and $1.34\pm0.09\times10^3/\mu l$ for normal mice (data from normal control group not shown). As shown in FIG. 1, leukocyte, neutrophil and lymphocyte counts rose steadily in CPM-treated mice to reach plateau values at day 8.

Administration of VTP 194310 at days −4 to −1 and at days 0 to 3 to mice treated with CPM (at day 0) improved leukocyte recovery in two ways. Leukocyte and neutrophil counts rose quicker in the VT P194310-treated mice as compared to the control group of leukopenic mice. Significant differences in recovery were observed as early as day 5 post-CPM. At day 8, the leukocyte and neutrophil counts in the blood of the VTP 194310-treated neutropenic mice were ~3 fold higher than counts in the mice treated with CPM alone (see FIG. 1). Administration of VTP 194310 to leukopenic mice at days 4 to 7 improved the numbers of leukocytes and neutrophils generated, but to an extent that was considerably less than when VTP 194310 was given earlier. Treatment of leukopenic mice with Peg-r-metHuG-CSF (at day 2) led to a sharp rise in the number of blood neutrophils. The levels of these cells peaked at day 7, and had declined by day 8 to numbers that were observed in the control group of leukopenic mice (see FIG. 1).

The leukopenic mice that were given VTP 194310, at days −4 to −1 and days 0 to 3, showed an increased number of lymphocytes in their blood as compared to the control leukopenic mice and these mice that had received Peg-r-metHuG-CSF. At day 8, the lymphocyte counts for the VTP194310-treated mice were $4.53\pm0.39\times10^3/\mu l$ (VTP 194310, days −4 to −1) and $4.49\pm0.52\times10^3/\mu l$ (VTP 194310, days 0 to 3) as compared to $2.38\pm0.26\times10^3/\mu l$ (p values<0.01) for control recovering mice.

EXAMPLE 2

Peripheral and Systemic Neutrophil and Lymphocyte Recovery in a Cyclophosphamide-Induced Mouse Model of Leukopenia It was examined whether the VTP 194310-driven neutrophil recovery in leukopenic mice was systemic by looking at the levels of neutrophils ($Gr1^{+ve}/CD11b^{+ve}$ cells) in the spleen and bone marrow. These mice were gavaged with VTP 194310 on days −1 to 2 in relation to CPM treatment.

Results

Figure 2A:
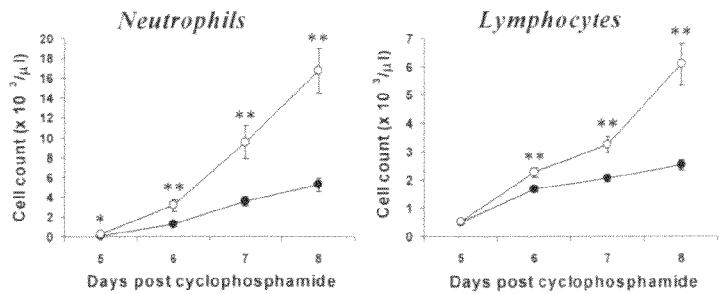
FIGS. 2A-2C are a graphical representation of the effects of VTP 194310 on the neutrophil counts and other parameters in a cyclophosphamide-induced leukopenic mouse model.
Figure 2B:
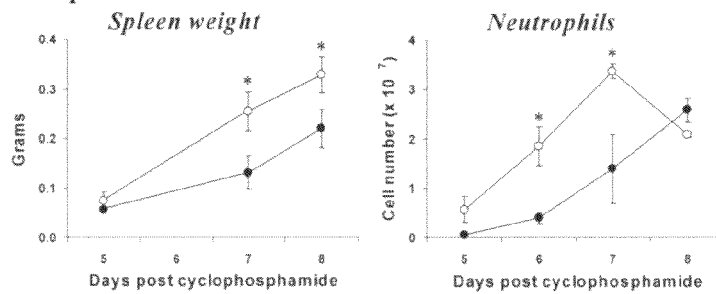
Figure 2C:
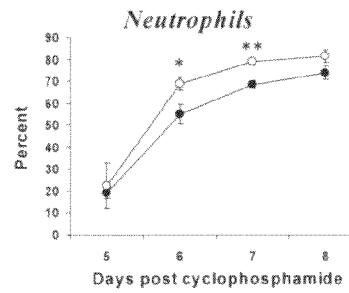

As the data shows, the neutrophil, and lymphocyte counts were significantly elevated in VTP 194310-treated mice at days 6 to 8, as compared to control recovering mice (see FIG. 2A). Spleen weight was increased at days 7 and 8 in the VTP 194310-treated mice as compared to the controls. The absolute number of $Gr-1^{+ve}/CD11b^{+ve}$ cells was significantly increased in the spleen of VTP 194310-treated mice at days 6 and 7 (see FIG. 2B). Additionally, immature granulocytes, identified as $Gr-1^{low}/CD11b^{+ve}$, were elevated in the spleen of VTP 194310-treated mice at days 6 and 7. The absolute number of these cells at day 7 was $0.93\pm0.02\times10^7$ in VTP194310-treated mice as compared to $0.46\pm0.13\times10^7$ in control mice (p=0.02). There was also an increased prevalence of $Gr-1^{+ve}/CD11b^{+ve}$ cells in the bone marrow of VTP 194310-treated mice (see FIG. 2C). Hence, neutrophil recovery that was provoked by VTP 194310 is systemic.

EXAMPLE 3

Measurement of the Protective Effect of VTP194310 Against *S. Aureus* Infection in Leukopenic Mice

*S. aureus* 29213 obtained from American Type Culture Collection (ATCC) (Rockville, Md.) was used to induce infections in leukopenic female BDF1 mice (20-22 g). *S. aureus* were cultured at 37° C. in Tryptic Soy broth until the mid-logarithmic phase of growth (optical density at 600 nm=0.3), harvested, and washed with PBS. The number of bacteria was enumerated by serial dilution with PBS, plating onto blood agar, and counting colony-forming units (CFU) 48 hours after incubation at 37° C. The suspension was adjusted to $10°$ CFU/ml.

Mice were rendered leukopenic by i.p. injection of CPM at 200 mg/kg. A lethal dose (LD) of *S. aureus* was determined by intravenous injections of $1\times10^3$ to $1\times10^8$ CFU to groups of 10 mice 4 days after CPM treatment. 10-day survivors were enumerated, and the $LD_{95}$ of *S. aureus* was calculated by Probit analysis. Treatment with VTP 194310 (at 1 mg/kg) was started one day before CPM and continued for 3 more days. Four days after CPM, the animals were infected intravenously with 4.1 and $2.5\times10^6$ CFU of *S. aureus* in 200 µl of PBS. Surviving animals were recorded daily for 14 days after the challenge. There were 12 mice per condition, and the significance of the protective effect of VTP 194310 was determined by the Logrank Test (GraphPad Prism version 3.0, GraphPad Software, Inc., San Diego, Calif.). All experiments were performed in compliance with relevant laws and institutional guidelines, and were approved by the Animal Care and Use Committee.

Results

Figure 3:
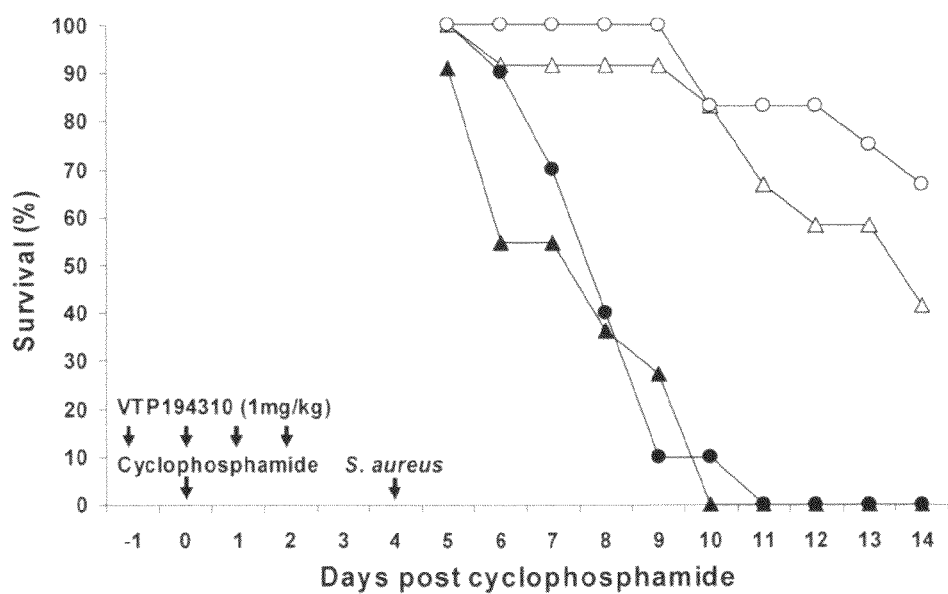
FIG. 3 is a graphical representation of the effect of VTP 194310 on the survival of leukopenic mice lethally infected with *Staphylococcus aureus*.

In this example, it was investigated whether the improved neutrophil recovery in the VTP 194310-treated leukopenic mice was able to protect them from infection by giving a lethal dose of *S. aureus* (see FIG. 3). VTP 194310 was given a day before CPM, at the same time as CPM and for two days after CPM, and *S. aureus* was injected at day 4 post-CPM. The mice given CPM and $4.1\times10^6$ CFU *S. aureus* had all died by day 10. Only 10% of the mice receiving the lower dose of *S. aureus* were alive, and these mice had died by day 11. At day 10, 83% of the mice that had received VTP 194310 and each of the doses of *S. aureus* were alive. The experiment was terminated at day 14, and 67% of the mice that had received VTP194310 and $2.5\times10^6$ CFU were alive, whereas 42% of mice that had received VTP 194310 and the higher dose of bacteria were alive. Accordingly, treatment with VTP 194310 as compared to controls had a very significant protective effect against *S. aureus* infection (p value=0.0031 for mice infected with $4.1\times10^6$ CFU *S. aureus*; p value<0.0001 for mice infected with $2.5\times10^6$ CFU *S. aureus*).

Survival of VTP 194310-treated mice given *S. aureus* was not due to activity of VTP 194310 against *S. aureus*. The compound was analyzed at an appropriate concentration in several assays for activity against *S. aureus* EMRSA-16 252 and *S. aureus* MSSA 476. Growth of bacteria on agar was not inhibited by the presence of 2 µM VTP 194310 incorporated into the agar, or when 50 µl of 2 µM VTP 194310 were added to an agar-well-diffusion assay. Furthermore, neither strain demonstrated any alteration in growth rate during growth in liquid culture in the presence of 2 µM VTP 194310.

EXAMPLE 4

Comparison of the Effects of Mono-Therapy and Combination Therapy of VTP 194310 and Pegylated-G-CSF on Neutrophil Recovery in CPM-Induced Neutropenic Mice Granulocyte-colony stimulating factor (G-CSF) is a key factor that drives recovery of neutrophils in neutropenia and is used clinically for the treatment of chemotherapy-induced severe neutropenia. It is therefore important to compare the effects of monotherapy VTP 194310, monotherapy G-CSF and the combined use of VTP 194310 with G-CSF. Monotherapy with VTP194310 (3 mg/kg, Days −1 to 1) and pegylated-G-CSF (10 µg/kg, Day 2) enhanced neutrophil recovery relative to control in neutropenic mice (150 mg/kg CPM). Combination treatment with these doses and regimens of VTP 194310 and pegylated-G-CSF further increased the rate of neutrophil recovery. The combined effect of VTP194310 and pegylated G-CSF in provoking a rise in blood neutrophils was slightly greater than additive. In addition, VTP 194310 together with G-CSF gave a rise in neutrophils that was sustained for longer than when G-CSF was used alone. These findings are commensurate with the proposition that VTP 194310 is acting with G-CSF during the recovery phase.
Formulations VTP 194310 DMSO stock solution was made by weighing out VTP 194310 and dissolved in DMSO (25 mg/1.33 ml DMSO). This stock solution was then mixed with Vehicle (39.2 ml Corn Oil+0.8 ml DMSO).

The 3.0 mg/kg VTP194310 solution was made by mixing 39.2 ml Corn Oil+0.8 ml VTP 194310 DMSO Stock.

The 1.0 mg/kg VTP194310 solution was made by diluting the VTP194310 DMSO Stock 1:3 with DMSO (e.g. 1 ml DMSO+0.5 ml 4310 Stock), and then combining 39.2 ml Corn Oil+0.8 ml of the diluted VTP194310 Stock.
Preparation of CPM Solutions:

The 150 mg/kg CPM solution was made by weighing out 187.5 mg 5-FU and mixing with 10 g saline.

Figure 4:
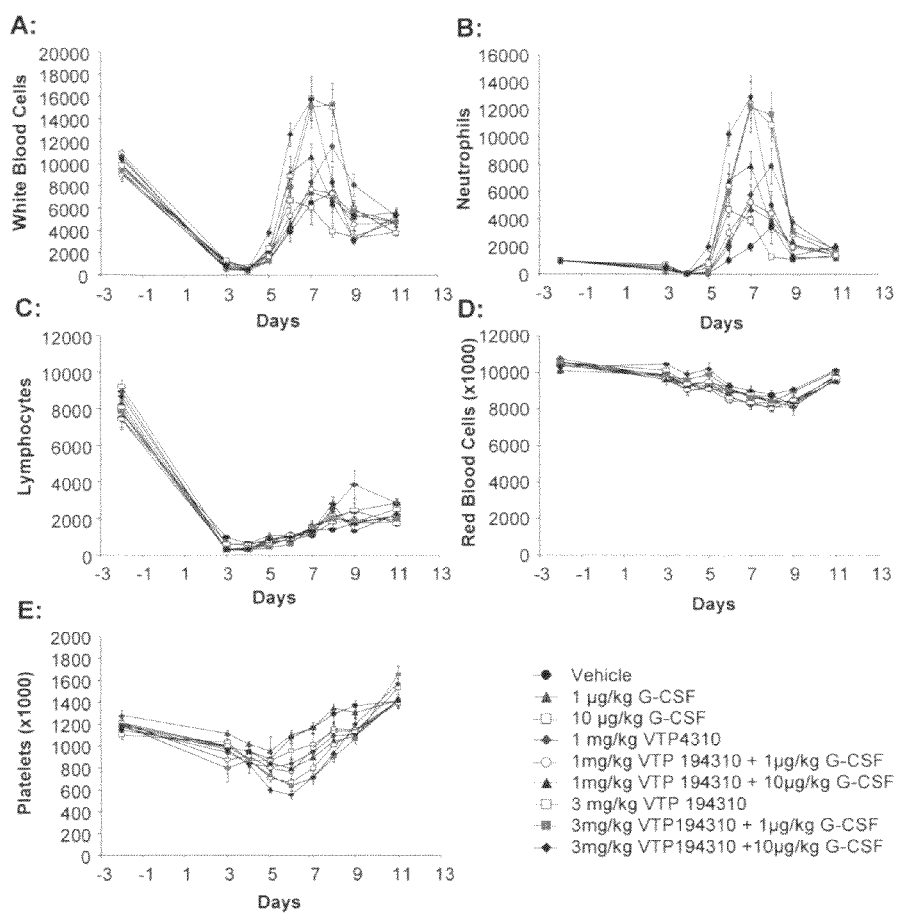
FIGS. 4A-4E are a graphical representation of the changes in total changes in total white blood cell (WBC), neutrophil, lymphocyte, red blood cell (RBC) and platelet numbers in mice that received VTP 194310 or/and PEG-G-CSF. Vehicle or VTP 194310 at 1 or 3 mg/kg/day was administrated orally on Days −1 to 1, 150 mg/kg CPM was given intraperitoneally on Day 0, and PEG-G-CSF was given subcutaneously on Day 2. Blood samples were collected as scheduled and the blood cell count was measured by Abbott Cell-DYN 3700. Data represent mean±SE of 7-8 mice. The units are numbers of cells or platelets per µl.
Figure 5:
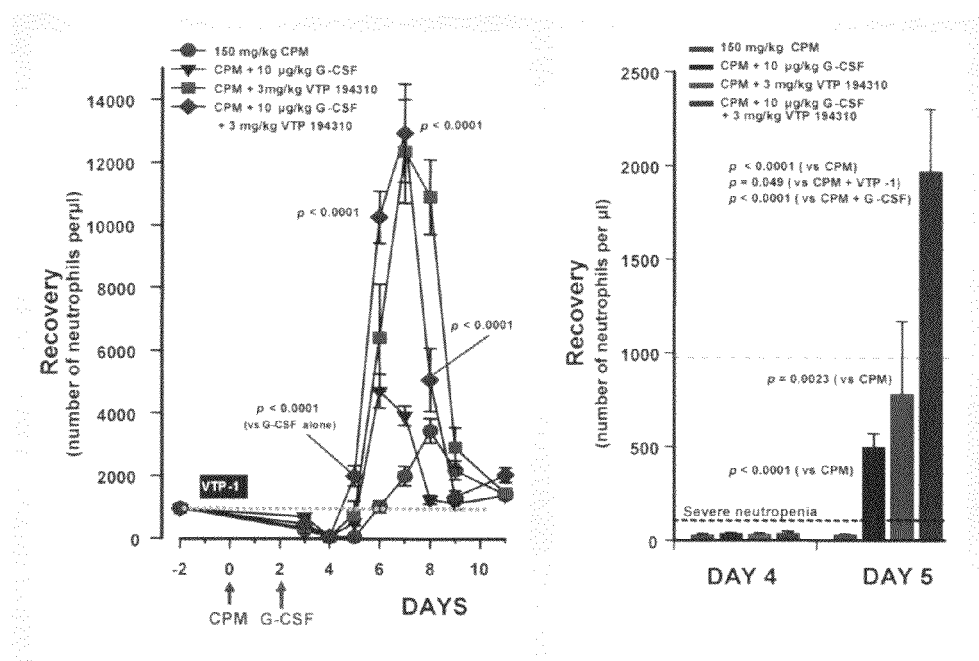
FIG. 5 is a graphical representation of the effect of treatment of neutropenia with a regimen of VTP 194310 and PEG-G-CSF, as compared to each agent alone, which further increased the rate of neutrophil recovery in neutropenic mice. Mice rendered neutropenic with 150 mg/kg CPM on Day 0 were given mono-therapy with VTP 194310 (3 mg/kg/day on Days −1 to 1) or PEG-G-CSF (10 g/kg on Day 2) and combination treatment with these doses. Data represent mean±SE of 7-8 mice. The p values for the statistical significance between treated groups are indicated. The units are numbers of cells or platelets per µl.

The 1 and 10 µg/kg PEG-G-CSF solutions were made by diluting 6 mg/ml stock with PBS.
Mice:

Male BDF1 mice (C57BlxDBA2), 7-8 weeks old, DOB: 1 Jun. 2006) were used in this experiment.
Blood Samples:

35 µl of blood (via the submandibular vein) were collected according to the scheduled time points or until the full recovery of blood cells and platelets. The blood samples were analyzed after 1:5 dilution with PBS saline containing 2% BSA (Fraction V) and 0.2 mM EDTA on the Hematology Analyzer Cell-DYN 3700 (Abbott Diagnostics).
Results Each group of mice were treated with vehicle, VTP 194310 at 3 mg/kg, PEG-G-CSF at 1 or 10 µg/kg, and CPM at 150 mg/kg. The mean numbers of total white blood cells (WBC), neutrophils, lymphocytes, red blood cells (RBC) and platelets and standard error (SE) for data obtained for each treated group are shown in FIG. 4. As shown in FIG. 4B and FIG. 5, monotherapy with VTP194310 at 1 or 3 mg/kg/day on Days −1 to 1 and PEG-G-CSF at 1 or 10 µg/kg on Day 2 enhanced neutrophil recovery relative to control in neutropenic mice (induced by 150 mg/kg CPM on Day 0). Combination treatments with these doses and regimens of VTP 194310 and PEG-G-CSF further increased the rate of neutrophil recovery as compared to the mono-therapy with either VTP 194310 or PEG-G-CSF. The combined effect of VTP 194310 and PEG-G-CSF in provoking a rise in blood neutrophils appeared additive or greater. In addition, VTP 194310 together with PEG-G-CSF gave a rise in neutrophils that was sustained for longer than when PEG-G-CSF was used alone: In conclusion, VTP194310 appears to be similarly effective to PEG-G-CSF at 10 µg/kg in enhancing neutrophil recovery in CPM-induced mouse model of neutropenia. Combination treatment with VTP 194310 and PEG-G-CSF further increased recovery.

EXAMPLE 5

Comparison of the Effects of Monotherapy and Combination Therapy of VTP 194310 and Pegylated-G-CSF on Neutrophil Recovery in 5-FU-Induced Neutropenic Mice Granulocyte-colony stimulating factor (G-CSF) is a key factor that drives recovery of neutrophils in neutropenia and is therefore used to treat chemotherapy-induced severe neutropenia in patients. It is important to compare the effect of monotherapy VTP 194310, monotherapy G-CSF and the combined effects of VTP 194310 with G-CSF. Here we carried out an experiment using a different mouse model of neutropenia, namely induced by administration of 150 mg/kg 5-FU. The goal was to investigate the effect of VTP 194310 and PEG-G-CSF in the 5-FU mouse model. Mono-therapy with VTP 194310 (3 mg/kg, days 2 to 4) improved the recovery of neutrophils as we observed previously. Monotherapy with PEG-G-CSF at 10 µg/kg administrated on different day (Days 5, 6, or 7) had little effect in enhancing neutrophil recovery. However, combination treatment with the same doses and regimens of VTP194310 and PEG-G-CSF significantly increased the rate of neutrophil recovery.
Formulations:

VTP194310 DMSO Stock solution was made by weighing out VTP194310 and dissolving it in DMSO (25 mg/1.33 ml DMSO).

The Vehicle solution was made by mixing 39.2 ml Corn Oil+0.8 ml DMSO.

The 3.0 mg/kg VTP194310 solution was made by mixing 39.2 ml Corn Oil+0.8 ml VTP 194310 DMSO Stock solution.

The 150 mg/kg 5-FU solution was made by weighing out 187.5 mg 5-FU and mixing it with 10 g saline.

Figure 6:
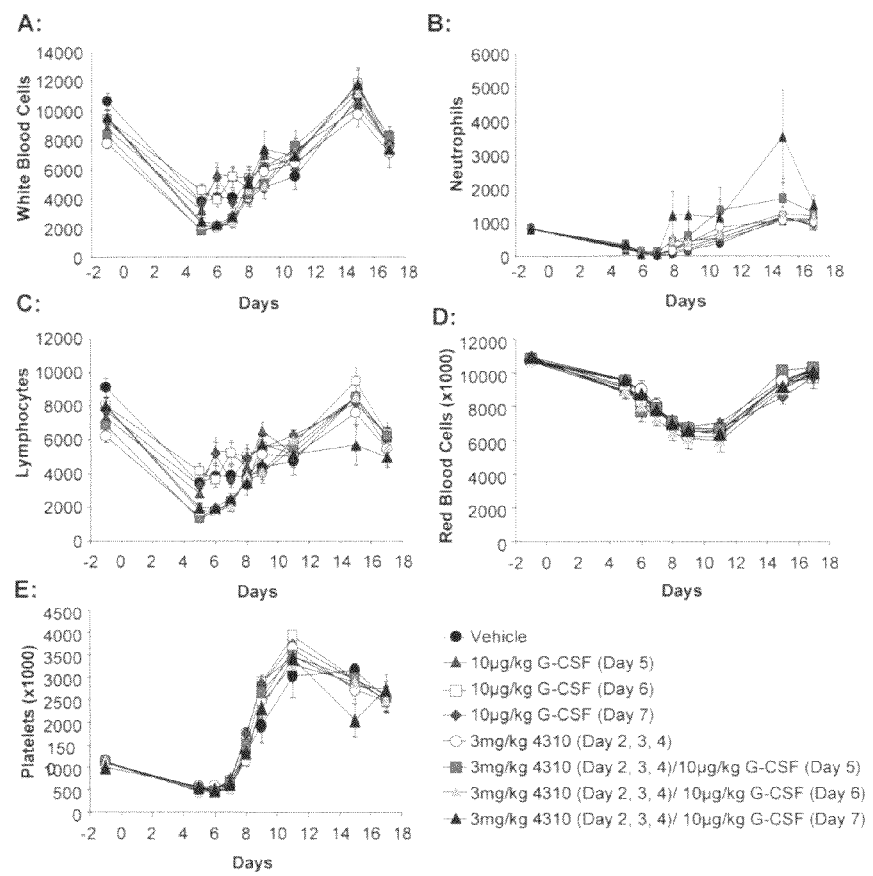
FIGS. 6A-6E are a graphical representation of the changes in total white blood cell (WBC), neutrophil, lymphocyte, red blood cell (RBC) and platelet numbers in mice that received VTP 194310 or/and PEG-G-CSF in 5-FU-induced mouse model of neutropenia. Vehicle or VTP194310 3 mg/kg/day was administrated orally on Days 2 to 4, 150 mg/kg 5-FU was given intravenously on Day 0, and PEG-G-CSF was given subcutaneously on Days 5, 6, or 7 as indicated. Blood samples were collected as scheduled and the blood cell count was measured by Abbott Cell-DYN 3700. Data represent mean±SE of 8 mice. The units are numbers of cells or platelets per µl.

The 10 µg/kg PEG-G-CSF solution was made by diluting 6 mg/ml stock with PBS.
Mice:

Male BDF1 mice (C57BlxDBA2), 9 weeks old, DOB: 26 Jun. 2006) were used in this experiment.
Results Each group of mice were treated with 150 mg/kg 5-FU intravenously on Day 0, vehicle or VTP194310 orally by gavage at 3 mg/kg/day on Days 2 to 4, and/or subcutaneously with PEG-G-CSF at 10 µg/kg on Days 5, 6, or 7 according to the regimens listed in the table. The mean numbers of total white blood cells (WBC), neutrophils, lymphocytes, red blood cells (RBC) and platelets and standard error (SE) of data obtained for each treated group are shown in FIG. 6. Administration of VTP194310 at 3 mg/kg/day for three days on Days 2 to 4 is more effective than PEG-G-CSF at 10 μg/kg given on Days 5, 6, or 7 in enhancing neutrophil recovery in the 5-FU-induced mouse model of neutropenia. Combination treatment with VTP 194310 and PEG-G-CSF appears to be more effective than either monotherapy with VTP 194310 or with PEG-G-CSF at provoking neutrophil recovery in this 5-FU-induced neutropenia model.

Figure 7:
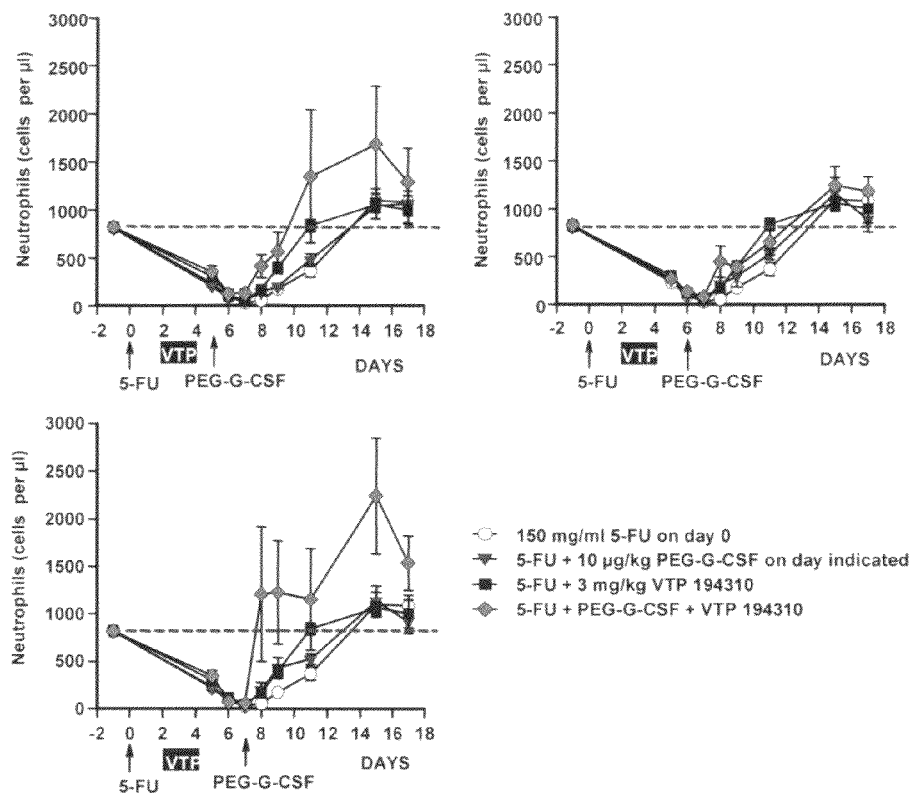
FIG. 7 is a graphical representation of a comparison of the effect of mono-therapy with VTP 194310 or peg-G-CSF and combination treatment on the recovery of neutrophils in 5-FU-induced neutropenic mice. Mice rendered neutropenic with 150 mg/kg 5-FU on day 0 were given mono-therapy with VTP 194310 (3 mg/kg/day on days 2 to 4) or peg-G-CSF (10 µg/kg) on day 5, 6, or 7 and combination treatment with these doses and regimens. Data represent mean±SE of 8 mice.

As shown in FIG. 6B and FIG. 7, monotherapy with VTP 194310 at 3 mg/kg/day on Days 2 to 4 improved the recovery of neutrophils, which was consistent with the results obtained previously (RT-06-34). Monotherapy with PEG-G-CSF at 10 μg/kg on Day 5, 6, or 7 showed little effect in enhancing neutrophil recovery relative to control in 5-FU neutropenic mice. Combination treatments with the same doses and regimens of VTP 194310 and PEG-G-CSF further increased the rate of neutrophil recovery as compared to the mono-therapy with VTP 194310.

EXAMPLE 6

Synthesis of VTP 194310 (Formerly Termed AGN 194310)

VTP 194310 has the following chemical structure:

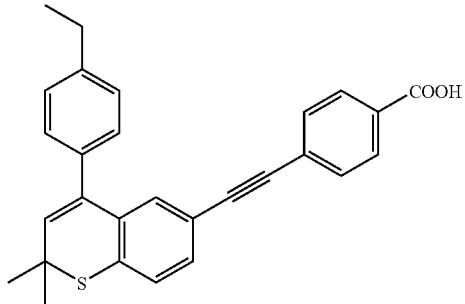 [SMILES: CCc1ccc(C2=CC(C)(C)Sc3ccc(C#Cc4ccc(C(=O)O)cc4)cc32)cc1]

This compound, 4-[[4-(4-ethylphenyl)-2,2-dimethyl-(2H)-thiochromen-6-yl]-ethynyl]-benzoic acid, may be synthesized using conventional organic synthetic means. The following reaction scheme is a currently preferred method of making this compound.

Step 1: A heavy-walled screw cap tube was charged with 3-methyl-2-butenoic acid (13.86 g, 138.4 mmol), 4-methoxy thiophenol (20.0 g, 138.4 mmol), and piperidine (3.45 g, 41.6 mmol). This mixture was heated to 10° C. for 32 hours, cooled to room temperature and dissolved in EtOAc (700 mL). The resulting solution was washed with 1 M aqueous HCl, H$_2$O, and saturated aqueous NaCl before being dried over Na$_2$SO$_4$. Concentration of the dry solution under reduced pressure afforded an oil which upon standing in the freezer provided a crystalline solid. 3-(4-methoxy-phenylsulfanyl)-3-methyl-butyric acid was isolated as pale-yellow crystals by washing the crystalline solid with pentane. (27.33 g, 82%). $^1$H NMR (300 MHz, CDCl$_3$) δ: 7.48 (2H, d, J=9.0 Hz), 6.89 (2H, d, J=8.9 Hz), 3.83 is (3H, s), 2.54 (2H, s), 1.40 (6H, s).

Step 2: To a solution of 3-(4-methoxy-phenylsulfanyl)-3-methyl-butyric acid (20.0 g, 83.2 mmol) in 250 mL of benzene at room temperature was added a solution of oxalyl chloride (15.84 g, 124.8 mmol) in 10 mL of benzene over 30 minutes. After 4 hours the solution was washed with ice cold 5% aqueous NaOH (CAUTION: a large volume of gas is released during this procedure), followed by ice cold H$_2$O and finally saturated aqueous NaCl. The solution was dried (Na$_2$SO$_4$) and concentrated under reduced pressure to give a clear yellow oil. This material was used without further purification in the next step. $^1$H NMR (300 MHz, CDCl$_3$) δ: 7.45 (2H, d, J=8.8 Hz), 6.90 (2H, d, J=8.8 Hz), 3.84 (3H, s), 3.12 (2H, s), 1.41 (6H, s).

Step 3: To a solution of the acyl chloride product of Step 2 (21.5 g, 83.2 mmol) in 250 mL of CH$_2$Cl$_2$ at 0° C. was added dropwise to a solution of SnCl$_4$ (21.7 g, 83.2 mmol) in 30 mL of CH$_2$Cl$_2$. After 2 hours the reaction was quenched by slow addition of 150 mL H$_2$O. The organic layer was washed with 1 M aqueous HCl, 5% aqueous NaOH, H$_2$O, and finally saturated aqueous NaCl before being dried over MgSO$_4$. Concentration under reduced pressure and vacuum distillation of the residual oil (Bulb-to-bulb, 125-135° C., 5 mm/Hg) afforded 14.48 g (78%) of 6-methoxy-2,2-dimethyl-thiochroman-4-one as a pale-yellow oil. $^1$H NMR (300 MHz, CDCl$_3$) δ: 7.62 (1H, d, J=2.9 Hz), 7.14 (1H, d, J=8.6 Hz), 7.03 (1H, dd, J=2.8, 8.3 Hz), 3.83 (3H, s), 2.87 (2H, s), 1.46 (6H, s).

Step 4: To a solution of 6-methoxy-2,2-dimethyl-thiochroman-4-one (6.0 g, 27 mmol) in 50 mL CH$_2$Cl$_2$ cooled to −23° C. was added BBr$_3$ (20.0 g, 80.0 mmol; 80.0 mL of a 1M solution in CH$_2$Cl$_2$) over a 20 minute period. After stirring for 5 hours at −23° C. the solution was cooled to −78° C. and quenched by the slow addition of 50 mL of H$_2$O. Upon warming to room temperature the aqueous layer was extracted with CH$_2$Cl$_2$ and the combined organic layers were washed with saturated aqueous NaHCO$_3$, H$_2$O, and saturated aqueous NaCl before being dried over MgSO$_4$. Removal of the solvents under reduced pressure gave a green-brown solid which upon recrystallization (Et$_2$O/hexanes) afforded 2.25 g (40%) of 6-hydroxy-2,2-dimethylthiochroman-4-one as a light brown solid. $^1$H NMR (300 MHz, CDCl$_3$) δ: 7.63 (1H, d, J=2.8 Hz), 7.15 (1H, d, J=8.5 Hz), 7.01 (1H, dd, J=2.8, 8.5 Hz), 2.87 (2H, s), 1.46 (6H, s).

Step 5: To a solution of 6-hydroxy-2,2-dimethylthiochroman-4-one (165.0 mg, 0.79 mmol) in 5.0 mL of anhydrous pyridine at 0° C. was added trifluoromethanesulfonic anhydride (245.0 mg, 0.87 mmol). After 4 hours at 0° C. the solution was concentrated and the residual oil dissolved in Et$_2$O, washed with H$_2$O followed by saturated aqueous NaCl, and dried over MgSO$_4$. Removal of the solvents under reduced pressure and column chromatography (5% EtOAc/hexanes) afforded 126.0 mg (47%) of 2,2-dimethyl-4-oxo-thiochroman-6-yl trifluoromethanesulfonate as a colorless solid. $^1$H NMR (300 MHz, CDCl$_3$) δ: 7.97 (1H, s), 7.32 (2H, s), 2.90 (2H, s), 1.49 (6H, s).

Step 6: A solution of 2,2-dimethyl-4-oxo-thiochroman-6-yl trifluoromethanesulfonate (2.88 g, 8.50 mmol) in 10 mL Et$_3$N and 20.0 mL DMF was purged with argon for 10 minutes. To this solution was added trimethylsilylacetylene (4.15 g, 42.0 mmol) and bis(triphenylphosphine)-palladium (II) chloride (298.0 mg, 0.425 mmol). The solution was heated to 95° C. for 5 hours, cooled to room temperature, and diluted with H$_2$O. Extraction with EtOAc was followed by washing the combined organic layers with H$_2$O and saturated aqueous NaCl and drying over MgSO$_4$. Concentration of the dry solution under reduced pressure and isolation of the product by column chromatography (3% EtOAc/hexanes) afforded 2.23 g (91%) of the 2,2-dimethyl-6-trimethylsilanylethynyl-thiochroman-4-one as an orange oil. $^1$H NMR (300 MHz, CDCl$_3$) δ: 8.18 (1H, d, J=1.9 Hz), 7.34 (1H, dd, J=1.9, 8.1 Hz), 7.15 (1H, d, J=8.1 Hz), 2.85 (2H, s), 1.45 (6H, s), 0.23 (9H, s).

Step 7: A solution of 2,2-dimethyl-6-trimethylsilanylethynylthiochroman-4-one (110.0 mg, 0.38 mmol) and K$_2$CO$_3$ (40.0 mg, 0.29 mmol) in 10.0 mL MeOH was stirred overnight at room temperature. The solution was diluted with H$_2$O and extracted with Et$_2$O. The combined organic layers were washed with H$_2$O and saturated aqueous NaCl and dried over MgSO₄. Removal of the solvent under reduced pressure afforded 81 mg (99%) of the 6-ethynyl-2,2-dimethylthiochroman-4-one as an orange oil. ¹H NMR (300 MHz, CDCl₃) δ: 8.20 (1H, d, J=1.9 Hz), 7.46 (1H, dd, J=1.9, 8.1 Hz), 7.18 (1H, d, J=8.1 Hz), 3.08 (1H, s), 2.86 (2H, s), 1.46 (6H, s).

Step 8: A solution of 6-ethynyl-2,2-dimethylthiochroman-4-one (82.0 mg, 0.38 mmol) and ethyl 4-iodobenzoate (104.9 mg, 0.38 mmol) in 5.0 mL Et₃N was purged with argon for 10 minutes. To this solution were added bis(triphenylphosphine)-palladium (II) chloride (88.0 mg, 0.12 mmol) and copper (I) iodide (22.9 mg, 0.12 mmol). After purging for an additional 5 minutes with argon, the solution was stirred overnight at room temperature. The reaction mixture was filtered through a pad of Celite using an Et₂O wash. Concentration of the filtrate under reduced pressure, followed by column chromatography of the residual solid, afforded 100 mg (72%) of ethyl 4-[(2,2-dimethyl-4-oxo-thiochroman-6-yl)ethynyl]-benzoate as a yellow solid. ¹H NMR (300 MHz, CDCl₃) δ: 8.25 (1H, d, J=1.8 Hz), 8.00 (2H, d, J=8.4 Hz), 7.55 (2H, d, J=8.4 Hz), 7.53 (1H, dd, J=1.8, 8.2 Hz), 7.21 (1H, d, J=8.2 Hz), 4.37 (2H, q, J=7.1 Hz), 2.88 (2H, s), 1.47 (6H, s), 1.39 (3H, t, J=7.1 Hz).

Step 9: A solution of sodium bis(trimethylsilyl)amide (1.12 g, 6.13 mmol) in 16.2 mL of THF was cooled to −78° C. and a solution of ethyl 4-(2,2-dimethyl-4-oxo-thiochroman-6-ylethynyl)-benzoate (1.86 g, 5.10 mmol) in 15.0 mL was added slowly. After 30 minutes a solution of 2-[N,N-bis(trifluoromethanesulfonyl)amino]-5-pyridine (2.40 g, 6.13 mmol) in 10 mL of THF was added. After 5 minutes the solution was warmed to room temperature and stirred overnight. The reaction was quenched by the addition of saturated aqueous NH₄Cl and extracted with EtOAc. The combined organic layers were washed with 5% aqueous NaOH and H₂O before being dried (MgSO₄) and concentrated under reduced pressure. Ethyl 4-((2,2-dimethyl-4-trifluoromethanesulfonyloxy-(2H)-thiochromen-6-yl)ethynyl)-benzoate, 1.53 g (61%), was isolated by column chromatography (2% EtOAc/hexanes) as a yellow solid. ¹H NMR (300 MHz, CDCl₃) δ: 8.03 (2H, d, J=8.4 Hz), 7.61 (1H, d, J=1.8 Hz), 7.59 (2H, d, J=8.4 Hz), 7.41 (1H, dd, J=1.8, 8.1 Hz), 7.29 (1H, d, J=8.1 Hz), 5.91 (1H, s), 4.39 (2H, q, J=7.1 Hz), 1.53 (6H, s), 1.41 (3H, t, J=7.1 Hz).

Step 10: A solution of 4-ethylbromobenzene (670.9 mg, 3.63 mmol) in 4.0 mL of THF was cooled to −78° C.; and tert-butyllithium (464.5 mg, 7.25 mmol, 4.26 mL of a 1.7M solution in pentane) was added to give a yellow solution. After 30 minutes a solution of ZnCl₂ (658.7 mg, 4.83 mmol) in 8.0 mL THF was slowly added via cannula. The resulting solution was warmed to room temperature and transferred via cannula to a solution of ethyl 4-(2,2-dimethyl-4-trifluoromethanesulfonyloxy-(2H)-thio-chromen-6-ylethynyl)-benzoate (1.20 g, 2.42 mmol) and tetrakis(triphenylphosphine)palladium(0) (111.7 mg, 0.097 mmol) in 8.0 mL THF. This solution was heated to 50° C. for 1 hour, cooled to room temperature, and the reaction quenched by the addition of saturated aqueous NH₄Cl. The solution was extracted with EtOAc and the combined organic layers were washed with H₂O and saturated aqueous NaCl before being dried (MgSO₄) and concentrated under reduced pressure. Ethyl 4-[[4-(4-ethylphenyl)-2,2-dimethyl-(2H)-thiochromen-6-yl]-ethynyl]-benzoate was isolated by column chromatography (5% EtOAc/hexanes) as a colorless oil.

¹H NMR (300 MHz, CDCl₃) δ: 7.99 (2H, d, J=8.2 Hz), 7.52 (2H, d, J=8.4 Hz), 7.40 (5H, m), 7.35 (2H, m), 5.85 (1H, s), 4.38 (2H, q, J=7.1 Hz), 2.72 (2H, q, J=7.6 Hz), 1.48 (6H, s), 1.40 (3H, t, J=7.1 Hz), 1.30 (3H, t, J=7.6 Hz).

Step 11: To a solution of ethyl 4-[[4-(4-ethylphenyl)-2,2-dimethyl-(2H)-thiochromen-6-yl]-ethynyl]-benzoate (940.0 mg, 2.08 mmol) in 10.0 mL THF and 5.0 mL EtOH was added NaOH (416.0 mg, 10.4 mmol, 5.2 mL of a 2M aqueous solution). The resulting solution was stirred overnight at room temperature. The reaction mixture was acidified with 10% aqueous HCl and extracted with EtOAc. The combined organic layers were washed with H₂O, saturated aqueous NaCl, and dried (Na₂SO₄) before removing the solvent under reduced pressure. The residual solid was recrystallized from CH₃CN to give 786.0 mg (89%) of 4-[[4-(4-ethylphenyl)-2,2-dimethyl-(2H)-thiochromen-6-yl]-ethynyl]-benzoic acid as a colorless solid. ¹H NMR (300 MHz, d₆-acetone) δ: 8.01 (2H, d, J=8.3 Hz), 7.60 (2H, d, J=8.5 Hz), 7.42 (2H, m), 7.29 (2H, m), 7.22 (3H, m), 5.94 (1H, s), 2.69 (2H, q, J=7.7 Hz), 1.47 (6H, s), 1.25 (3H, t, J=7.7 Hz). This compound, the final desired product, was termed VTP 194310.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

Any and all patents, patent applications, and other publications referred to in this application are incorporated herein by reference in their entirety.

What is claimed is:

1. A method for treating chemotherapy and/or radiation therapy side effects in a mammal undergoing chemotherapy and/or radiation therapy, the method comprising a step of administering to the mammal a therapeutically effective amount of at least one Retinoic Acid Receptor (RAR) antagonist or a RAR inverse agonist which binds to receptors of the RARα, RARβ and RARγ subtypes, wherein the RAR antagonist or RAR inverse agonist has the chemical structure according to Formula (I):

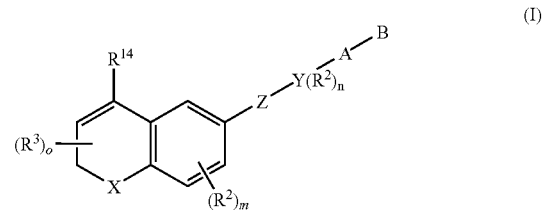

or a pharmaceutically acceptable salt thereof;
wherein X is S or O
R² independently are hydrogen, a lower alkyl of 1 to 6 carbons, F, Cl, Br, I, CF₃, fluoro substituted alkyl of 1 to 6 carbons, OH, SH, alkoxy of 1 to 6 carbons, or alkylthio of 1 to 6 carbons;
R³ independently is hydrogen, lower alkyl of 1 to 6 carbons, or F;
m is an integer having the value of 0-3;
n is an integer having the value of 0-4;
o is an integer having the value of 0-3;
Z is —CONR¹—, —CSNR¹—, —NR¹CO—, —NR¹CS—, —C≡C—, —C=C—, —N=N—, —N=CR¹—, —CR¹=N—, —COO—, —OCO—; —OSO—; —OCS—, or —(CR¹=CR¹)ₙ'—, where n' is an integer from 0 to 5;
Y is a phenyl or naphthyl group, or a heteroaryl selected from a group consisting of pyridyl, thienyl, furyl, pyridazinyl, pyrimidinyl, pyrazinyl, thiazolyl, oxazolyl, imidazolyl, and pyrrazolyl, the phenyl and heteroaryl groups being optionally substituted with one or two $R^2$ groups, or when Z is $-(CR^1=CR^1)_{n'}-$ and n' is 3, 4, or 5, then Y represents a direct valence bond between said $(CR^2=CR^2)_{n'}$ group and A;

A is $(CH_2)_q$, where q is 0-5, a lower branched chain alkyl having 3 to 6 carbons, cycloalkyl having 3 to 6 carbons, alkenyl having 2 to 6 carbons and 1 or 2 double bonds, or alkynyl having 2-6 carbons and 1 or 2 triple bonds;

B is hydrogen, COOH or a pharmaceutically acceptable salt thereof, $COOR^8$, $CONR^9R^{10}$, $CH_2OH$, $CH_2OR^{11}$, $CH_2OCOR^{11}$, CHO, $CH(OR^{12})_2$, $CHOR^{13}O$, $-COR^7$, $CR^7(OR^{12})_2$, $CR^7OR^{12}O$, or a tri-lower alkylsilyl;

$R^7$ is an alkyl, cycloalkyl or alkenyl group containing 1 to 5 carbons;

$R^8$ is an alkyl group of 1 to 10 carbons or trimethylsilylalkyl where the alkyl group has 1 to 10 carbons, a cycloalkyl group of 3 to 10 carbons, phenyl or a lower alkylphenyl;

$R^9$ and $R^{10}$ independently are hydrogen, an alkyl group of 1 to 10 carbons, a cycloalkyl group of 3 to 10 carbons, phenyl, or a lower alkylphenyl;

$R^{11}$ is a lower alkyl, phenyl, or lower alkylphenyl;

$R^{12}$ is a lower alkyl;

$R^{13}$ is a divalent alkyl radical of 2 to 5 carbons;

$R^{14}$ is $(R^{15})_r$-phenyl, $(R^{15})_r$-naphthyl, or $(R^{15})_r$-heteroaryl, wherein the heteroaryl group has 1 to 3 heteroatoms selected from the group consisting of O, S and N, and r is an integer having the values of 0-5; and $R^{15}$ is independently H, F, Cl, Br, I, $NO_2$, $N(R^8)_2$, $N(R^8)COR^8$, $NR^8CON(R^8)_2$, OH, $OCOR^8$, $OR^B$, CN, an alkyl group having 1 to 10 carbons, a fluoro substituted alkyl group having 1 to 10 carbons, an alkenyl group having 2 to 10 carbons and 1 to 3 double bonds, an alkynyl group having 2 to 10 carbons and 1 to 3 triple bonds, or a trialkylsilyl or trialkylsilyloxy group, where the alkyl groups independently have 1 to 6 carbons.

2. The method of claim 1, wherein the RAR antagonist or RAR inverse agonist is effective to increase mature neutrophil production in the mammal.

3. A method for increasing platelet production in a mammal in need thereof, the method comprising a step of administering to the mammal an effective amount of at least one RAR antagonist or a RAR inverse agonist which binds to receptors of the RARα, RARβ and RARγ subtypes, wherein the RAR antagonist or RAR inverse agonist has the chemical structure according to Formula (I):

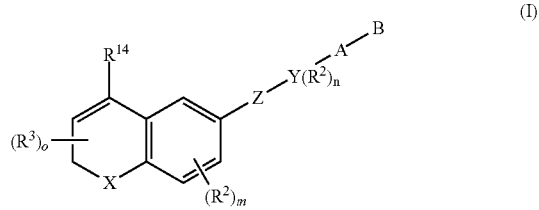

(I)

or a pharmaceutically acceptable salt thereof;
wherein X is S or O;

$R^2$ independently are hydrogen, a lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R^3$ independently is hydrogen, lower alkyl of 1 to 6 carbons, or F;

m is an integer having the value of 0-3;

n is an integer having the value of 0-4;

o is an integer having the value of 0-3;

Z is $-CONR^1-$, $-CSNR^1-$, $-NR^1CO-$, $-NR^1CS-$, $-C\equiv C-$, $-C=C-$, $-N=N-$, $-N=CR^1-$, $-CR^1=N-$, $-COO-$, $-OCO-$; $-OSO-$; $-OCS-$, or $-(CR^1=CR^1)_{n'}-$, where n' is an integer from 0 to 5;

Y is a phenyl or naphthyl group, or a heteroaryl selected from a group consisting of pyridyl, thienyl, furyl, pyridazinyl, pyrimidinyl, pyrazinyl, thiazolyl, oxazolyl, imidazolyl, and pyrrazolyl, the phenyl and heteroaryl groups being optionally substituted with one or two $R^2$ groups, or when Z is $-(CR^1=CR^1)_{n'}-$ and n' is 3, 4, or 5, then Y represents a direct valence bond between said $(CR^2=CR^2)_{n'}$ group and A;

A is $(CH_2)_q$, where q is 0-5, a lower branched chain alkyl having 3 to 6 carbons, cycloalkyl having 3 to 6 carbons, alkenyl having 2 to 6 carbons and 1 or 2 double bonds, or alkynyl having 2-6 carbons and 1 or 2 triple bonds;

B is hydrogen, COOH or a pharmaceutically acceptable salt thereof, $COOR^8$, $CONR^9R^{10}$, $CH_2OH$, $CH_2OR^{11}$, $CH_2OCOR^{11}$, CHO, $CH(OR^{12})_2$, $CHOR^{13}O$, $-COR^7$, $CR^7(OR^{12})_2$, $CR^7OR^{12}O$, or a tri-lower alkylsilyl;

$R^7$ is an alkyl, cycloalkyl or alkenyl group containing 1 to 5 carbons;

$R^8$ is an alkyl group of 1 to 10 carbons or trimethylsilylalkyl where the alkyl group has 1 to 10 carbons, a cycloalkyl group of 3 to 10 carbons, phenyl or a lower alkylphenyl;

$R^9$ and $R^{10}$ independently are hydrogen, an alkyl group of 1 to 10 carbons, a cycloalkyl group of 3 to 10 carbons, phenyl, or a lower alkylphenyl;

$R^{11}$ is a lower alkyl, phenyl, or lower alkylphenyl;

$R^{12}$ is a lower alkyl;

$R^{13}$ is a divalent alkyl radical of 2 to 5 carbons;

$R^{14}$ is $(R^{15})_r$-phenyl, $(R^{15})_r$-naphthyl, or $(R^{15})_r$-heteroaryl, wherein the heteroaryl group has 1 to 3 heteroatoms selected from the group consisting of O, S and N, and r is an integer having the values of 0-5; and $R^{15}$ is independently H, F, Cl, Br, I, $NO_2$, $N(R^8)_2$, $N(R^8)COR^8$, $NR^8CON(R^8)_2$, OH, $OCOR^8$, $OR^8$, CN, an alkyl group having 1 to 10 carbons, a fluoro substituted alkyl group having 1 to 10 carbons, an alkenyl group having 2 to 10 carbons and 1 to 3 double bonds, an alkynyl group having 2 to 10 carbons and 1 to 3 triple bonds, or a trialkylsilyl or trialkylsilyloxy group, where the alkyl groups independently have 1 to 6 carbons.

4. The method of claim 1, wherein the side effect is neutropenia.

5. The method of claim 1, wherein the side effect is leukopenia or thrombocytopenia.

6. The method of claim 1 wherein the RAR antagonist or RAR inverse agonist has the chemical structure according to Formula II:

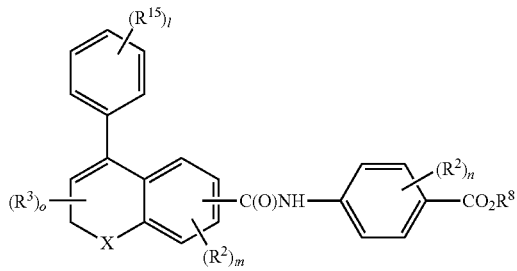

(II)

or a pharmaceutically acceptable salt thereof;
wherein X is O;
$R^2$ is a lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;
n is an integer having the value of 0-4;
m is an integer having the value of 0-3;
o is an integer having the value of 0-3;
$R^3$ is a lower alkyl of 1 to 6 carbons or F;
$R^8$ is an alkyl group of 1 to 10 carbons, trimethylsilylalkyl wherein the alkyl group has 1 to 10 carbons, or a cycloalkyl group of 3 to 10 carbons, phenyl, or a lower alkylphenyl;
$R^{15}$ independently is H, F, Cl, Br, I, $NO_2$, $N(R^8)_2$, $COR^8$, $NR^8CON(R^8)_2$, $OCOR^8$, $OR^8$, CN, an alkyl group having 1 to 10 carbons, fluoro substituted alkyl group having 1 to 10 carbons, an alkenyl group having 2 to 10 carbons and 1 to 3 double bonds, an alkynyl group having 2 to 10 carbons and 1 to 3 triple bonds, or a trialkylsilyl or trialkylsilyloxy group, where the alkyl groups independently have 1 to 6 carbons;
t is an integer having the values of 0-5; and
the CONH group is in the 6 or 7 position of the benzopyran and of the dihydronaphthaline ring.

7. The method of claim 1, wherein the RAR antagonist or RAR inverse agonist has the chemical structure according to Formula III:

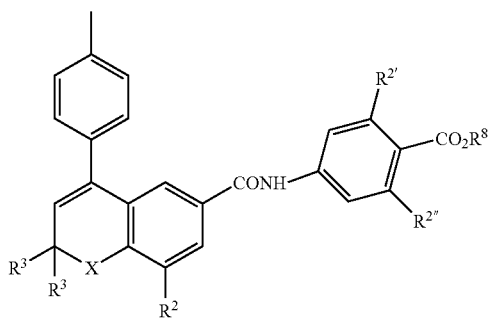

(III)

or a pharmaceutically acceptable salt thereof;
wherein X is O;
$R^2$ is H or Br;
$R^{2'}$ and $R^{2''}$ are independently H or F;
each $R^3$ is independently H or $CH_3$; and
$R^8$ is H, or a $C_1$-$C_6$ alkyl.

8. The method of claim 1, wherein the RAR antagonist or RAR inverse agonist has the chemical structure according to Formula V:

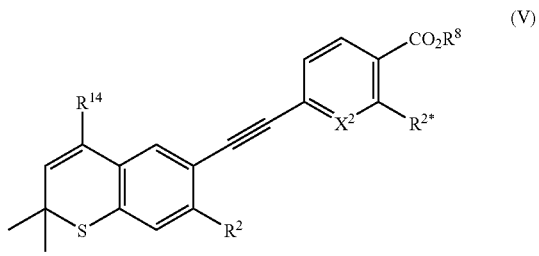

(V)

or pharmaceutically acceptable salts thereof;
wherein $X^2$ is CH or N;
$R^2$ is H, F or $CH_3$,
$R^{2'}$ is H or F;
$R^8$ is H, or $C_1$-$C_6$ alkyl; and
$R^{14}$ is selected from the group consisting of: phenyl, 4-(lower alkyl)phenyl, 5-(loweralkyl)-2-thienyl, and 6-(lower-alkyl)-3-pyridyl, where lower alkyl has 1 to 6 carbons.

9. The method of claim 1, wherein the RAR antagonist or RAR inverse agonist has the chemical structure according to Formula VI:

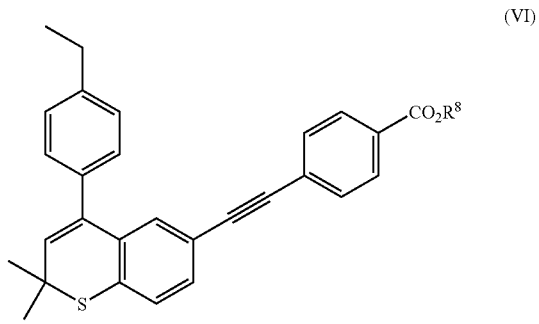

(VI)

or pharmaceutically acceptable salts thereof;
wherein $R^8$ is H, or a $C_1$-$C_6$ alkyl.

10. The method of claim 1, wherein the RAR antagonist or RAR inverse agonist has the chemical structure:

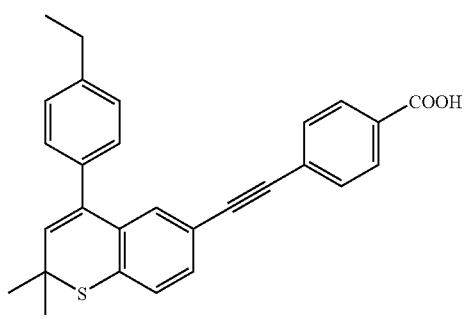 [SMILES: CCc1ccc(C2=CC(C)(C)Sc3ccc(C#Cc4ccc(C(=O)O)cc4)cc32)cc1]

or pharmaceutically acceptable salts thereof.

* * * * *